(12) United States Patent
Blahut

(10) Patent No.: US 11,555,172 B2
(45) Date of Patent: Jan. 17, 2023

(54) CELL AND TISSUE CULTURE CONTAINER

(71) Applicant: Histogenics Corporation, Waltham, MA (US)

(72) Inventor: Eric Blahut, Quincy, MA (US)

(73) Assignee: Ocugen, Inc., Malvern, PA (US)

(*) Notice: Subject to any disclaimer, the term of this patent is extended or adjusted under 35 U.S.C. 154(b) by 1106 days.

(21) Appl. No.: 16/131,234

(22) Filed: Sep. 14, 2018

(65) Prior Publication Data

US 2019/0010439 A1 Jan. 10, 2019

Related U.S. Application Data

(62) Division of application No. 14/558,080, filed on Dec. 2, 2014, now Pat. No. 10,077,420.

(51) Int. Cl.
*C12M 3/00* (2006.01)
*C12M 1/00* (2006.01)
*C12M 1/04* (2006.01)
*C12M 1/12* (2006.01)
*C12M 1/42* (2006.01)

(52) U.S. Cl.
CPC ............ *C12M 23/24* (2013.01); *C12M 21/08* (2013.01); *C12M 23/22* (2013.01); *C12M 23/34* (2013.01); *C12M 23/38* (2013.01); *C12M 25/14* (2013.01); *C12M 35/08* (2013.01)

(58) Field of Classification Search
CPC ....... C12M 25/14; C12M 23/34; C12M 23/24
See application file for complete search history.

(56) References Cited

U.S. PATENT DOCUMENTS

| | | |
|---|---|---|
| 3,400,199 A | 9/1968 | Balassa |
| 3,476,855 A | 11/1969 | Balassa |
| 3,478,146 A | 11/1969 | Balassa |
| 3,551,566 A | 12/1970 | Thiels |
| 3,772,432 A | 11/1973 | Balassa |
| 3,791,930 A | 2/1974 | Saxholm |
| 3,867,728 A | 2/1975 | Stubstad et al. |
| 3,966,908 A | 6/1976 | Balassa |
| 4,060,081 A | 11/1977 | Yannas et al. |

(Continued)

FOREIGN PATENT DOCUMENTS

| | | |
|---|---|---|
| EP | 0068149 A2 | 1/1983 |
| EP | 0075444 A2 | 3/1983 |

(Continued)

OTHER PUBLICATIONS

European Search Opinion and Extended European Search Report in Application No. 15865074.7, dated Jun. 22, 2018.

(Continued)

*Primary Examiner* — Nathan A Bowers
(74) *Attorney, Agent, or Firm* — Don D. Cha; HDC Intellectual Property Law, LLP

(57) ABSTRACT

The invention generally relates to containers for cell and tissue culturing with multiple compartments in fluid communication with each other to provide a common culture environment in each of the compartments while maintaining physical separation of cells and tissue therein. The invention further relates to culture containers providing a sterile culture environment with detachably coupleable lids and open access to each compartment within a container.

17 Claims, 8 Drawing Sheets

(56) References Cited

U.S. PATENT DOCUMENTS

| | | |
|---|---|---|
| 4,172,128 A | 10/1979 | Thiele |
| 4,182,655 A | 1/1980 | Hartmeier |
| 4,201,845 A | 5/1980 | Feder et al. |
| 4,280,954 A | 7/1981 | Yannas et al. |
| 4,296,100 A | 10/1981 | Franco |
| 4,350,629 A | 9/1982 | Yannas et al. |
| 4,378,347 A | 3/1983 | Franco |
| 4,394,370 A | 7/1983 | Jefferies |
| 4,400,833 A | 8/1983 | Kurland |
| 4,442,655 A | 4/1984 | Stroetmann |
| 4,448,718 A | 5/1984 | Yannas et al. |
| 4,458,678 A | 7/1984 | Yannas et al. |
| 4,479,271 A | 10/1984 | Botesky et al. |
| 4,501,289 A | 2/1985 | Bagby |
| 4,505,286 A | 3/1985 | Yannas et al. |
| 4,522,753 A | 6/1985 | Yannas et al. |
| 4,522,811 A | 6/1985 | Eppstein et al. |
| 4,582,865 A | 4/1986 | Balazs et al. |
| 4,600,574 A | 7/1986 | Lindner et al. |
| 4,609,551 A | 9/1986 | Caplan et al. |
| 4,627,853 A | 12/1986 | Campbell et al. |
| 4,642,120 A | 2/1987 | Nevo et al. |
| 4,656,137 A | 4/1987 | Balassa |
| 4,681,763 A | 7/1987 | Nathanson et al. |
| 4,683,195 A | 7/1987 | Mullis et al. |
| 4,683,202 A | 7/1987 | Mullis |
| 4,713,448 A | 12/1987 | Balazs et al. |
| 4,736,866 A | 4/1988 | Leder et al. |
| 4,757,017 A | 7/1988 | Cheung |
| 4,776,173 A | 10/1988 | Kamarei et al. |
| 4,776,853 A | 10/1988 | Klement et al. |
| 4,795,467 A | 1/1989 | Piez et al. |
| 4,801,299 A | 1/1989 | Brendel et al. |
| 4,837,379 A | 6/1989 | Weinberg |
| 4,846,835 A | 7/1989 | Grande |
| 4,851,354 A | 7/1989 | Winston et al. |
| 4,870,009 A | 9/1989 | Evans et al. |
| 4,873,191 A | 10/1989 | Wagner et al. |
| 4,873,192 A | 10/1989 | Kunkel |
| 4,880,429 A | 11/1989 | Stone |
| 4,880,610 A | 11/1989 | Constantz |
| 4,902,508 A | 2/1990 | Badylak et al. |
| 4,904,259 A | 2/1990 | Itay |
| 4,912,032 A | 3/1990 | Hoffman et al. |
| 4,932,973 A | 6/1990 | Gendler |
| 4,950,296 A | 8/1990 | McIntyre |
| 4,950,483 A | 8/1990 | Ksander et al. |
| 4,955,911 A | 9/1990 | Frey et al. |
| 4,963,146 A | 10/1990 | Li |
| 4,963,489 A | 10/1990 | Naughton et al. |
| 4,965,188 A | 10/1990 | Mullis et al. |
| 4,971,954 A | 11/1990 | Brodsky et al. |
| 4,976,738 A | 12/1990 | Frey et al. |
| 4,978,355 A | 12/1990 | Frey et al. |
| 4,981,783 A | 1/1991 | Augenlicht |
| 4,994,559 A | 2/1991 | Moscatelli et al. |
| 5,002,071 A | 3/1991 | Harrell |
| 5,002,583 A | 3/1991 | Pitaru et al. |
| 5,007,934 A | 4/1991 | Stone |
| 5,010,892 A | 4/1991 | Colvin et al. |
| 5,032,508 A | 7/1991 | Naughton et al. |
| 5,041,138 A | 8/1991 | Vacanti et al. |
| 5,053,049 A | 10/1991 | Campbell |
| 5,053,050 A | 10/1991 | Itay |
| 5,067,963 A | 11/1991 | Khouri et al. |
| 5,067,964 A | 11/1991 | Richmond et al. |
| 5,071,436 A | 12/1991 | Huc et al. |
| 5,073,373 A | 12/1991 | O'Leary et al. |
| 5,084,051 A | 1/1992 | Tormala et al. |
| 5,087,963 A | 2/1992 | Kaneda et al. |
| 5,092,867 A | 3/1992 | Harms et al. |
| 5,092,887 A | 3/1992 | Gendler |
| 5,118,512 A | 6/1992 | O'Leary et al. |
| 5,152,791 A | 10/1992 | Hakamatsuka et al. |
| 5,155,214 A | 10/1992 | Baird et al. |
| 5,191,067 A | 3/1993 | Lappi et al. |
| 5,195,892 A | 3/1993 | Gersberg |
| 5,206,023 A | 4/1993 | Hunziker |
| 5,206,028 A | 4/1993 | Li |
| 5,226,914 A | 7/1993 | Capian et al. |
| 5,227,147 A | 7/1993 | Yoshimura et al. |
| 5,236,456 A | 8/1993 | O'Leary et al. |
| 5,256,140 A | 10/1993 | Fallick |
| 5,256,476 A | 10/1993 | Tanaka et al. |
| 5,260,420 A | 11/1993 | Burouf-Radosevich et al. |
| 5,270,197 A | 12/1993 | Yayon et al. |
| 5,270,300 A | 12/1993 | Hunziker |
| 5,275,826 A | 1/1994 | Badylak et al. |
| 5,281,265 A | 1/1994 | Liu |
| 5,281,422 A | 1/1994 | Badylak et al. |
| 5,284,155 A | 2/1994 | Treadwell et al. |
| 5,290,558 A | 3/1994 | O'Leary et al. |
| 5,298,254 A | 3/1994 | Prewett et al. |
| 5,302,702 A | 4/1994 | Seddon et al. |
| 5,306,304 A | 4/1994 | Gendler |
| 5,306,311 A | 4/1994 | Stone et al. |
| 5,306,500 A | 4/1994 | Rhee et al. |
| 5,310,883 A | 5/1994 | Seddon et al. |
| 5,314,476 A | 5/1994 | Prewett et al. |
| 5,326,357 A | 7/1994 | Kandel |
| 5,329,846 A | 7/1994 | Bonutti |
| 5,336,616 A | 8/1994 | Livesey et al. |
| 5,338,772 A | 8/1994 | Bauer et al. |
| 5,352,463 A | 10/1994 | Badylak et al. |
| 5,352,589 A | 10/1994 | Bergonzoni et al. |
| 5,354,557 A | 10/1994 | Oppermann et al. |
| 5,356,629 A | 10/1994 | Sander et al. |
| 5,356,883 A | 10/1994 | Kuo et al. |
| 5,368,858 A | 11/1994 | Hunziker |
| 5,372,821 A | 12/1994 | Badylak et al. |
| 5,380,328 A | 1/1995 | Morgan |
| 5,410,016 A | 4/1995 | Hubbell et al. |
| 5,411,885 A | 5/1995 | Marx |
| 5,425,769 A | 6/1995 | Snyders, Jr. |
| 5,439,684 A | 8/1995 | Prewett et al. |
| 5,439,818 A | 8/1995 | Fiddes et al. |
| 5,443,950 A | 8/1995 | Naughton et al. |
| 5,445,833 A | 8/1995 | Badylak et al. |
| 5,464,439 A | 11/1995 | Gendler |
| 5,466,462 A | 11/1995 | Rosenthal et al. |
| 5,471,893 A | 12/1995 | Newbigging |
| 5,474,987 A | 12/1995 | Cohen et al. |
| 5,475,052 A | 12/1995 | Rhee et al. |
| 5,491,220 A | 2/1996 | Seddon et al. |
| 5,496,722 A | 3/1996 | Goodwin et al. |
| 5,507,813 A | 4/1996 | Dowd et al. |
| 5,510,396 A | 4/1996 | Prewett et al. |
| 5,512,460 A | 4/1996 | Nauro et al. |
| 5,513,682 A | 5/1996 | Morse et al. |
| 5,516,532 A | 5/1996 | Atala et al. |
| 5,516,533 A | 5/1996 | Badylak et al. |
| 5,522,753 A | 6/1996 | McGraw |
| 5,545,222 A | 8/1996 | Bonutti |
| 5,549,904 A | 8/1996 | Juergensen et al. |
| 5,554,389 A | 9/1996 | Badylak et al. |
| 5,556,430 A | 9/1996 | Gendler |
| 5,565,519 A | 10/1996 | Rhee et al. |
| 5,569,272 A | 10/1996 | Reed et al. |
| 5,569,584 A | 10/1996 | Augenlicht |
| 5,571,721 A * | 11/1996 | Turner ............ B29C 66/131 359/398 |
| 5,571,895 A | 11/1996 | Kurokawa et al. |
| 5,576,288 A | 11/1996 | Lappi et al. |
| 5,604,293 A | 2/1997 | Fiddes et al. |
| 5,606,793 A | 3/1997 | Gross et al. |
| 5,607,474 A | 3/1997 | Athanasiou et al. |
| 5,614,496 A | 3/1997 | Dunstan et al. |
| 5,614,587 A | 3/1997 | Rhee et al. |
| 5,616,568 A | 4/1997 | Pouyani et al. |
| 5,618,551 A | 4/1997 | Tardy et al. |
| 5,618,925 A | 4/1997 | Dupont et al. |
| 5,622,928 A | 4/1997 | Naruo et al. |
| 5,624,463 A | 4/1997 | Stone et al. |
| 5,629,191 A | 5/1997 | Cahn |

(56) References Cited

U.S. PATENT DOCUMENTS

| | | |
|---|---|---|
| 5,630,842 A | 5/1997 | Brodniewicz |
| 5,630,982 A | 5/1997 | Boring |
| 5,631,011 A | 5/1997 | Wadstrom |
| 5,632,745 A | 5/1997 | Schwartz |
| 5,650,176 A | 7/1997 | Lee et al. |
| 5,653,730 A | 8/1997 | Hammerslag |
| 5,656,492 A | 8/1997 | Glowacki et al. |
| 5,656,598 A | 8/1997 | Dunstan et al. |
| 5,662,710 A | 9/1997 | Bonutti |
| 5,676,976 A | 10/1997 | Lee et al. |
| 5,679,637 A | 10/1997 | Lappi et al. |
| 5,681,353 A | 10/1997 | Li et al. |
| 5,683,461 A | 11/1997 | Lee et al. |
| 5,686,431 A | 11/1997 | Cohen et al. |
| 5,695,998 A | 12/1997 | Badylak et al. |
| 5,700,476 A | 12/1997 | Rosenthal et al. |
| 5,700,774 A | 12/1997 | Hattersley et al. |
| 5,707,962 A | 1/1998 | Chen et al. |
| 5,713,374 A | 2/1998 | Pachence et al. |
| 5,718,413 A | 2/1998 | Walter et al. |
| 5,723,331 A | 3/1998 | Tubo et al. |
| 5,728,159 A | 3/1998 | Stroever et al. |
| 5,733,337 A | 3/1998 | Carr, Jr. et al. |
| 5,733,564 A | 3/1998 | Lehtinen |
| 5,736,132 A | 4/1998 | Juergensen et al. |
| 5,736,372 A | 4/1998 | Vacanti et al. |
| 5,736,396 A | 4/1998 | Bruder et al. |
| 5,749,874 A | 5/1998 | Schwartz |
| 5,755,791 A | 5/1998 | Whitson et al. |
| 5,759,190 A | 6/1998 | Vibe-Hansen et al. |
| 5,763,416 A | 6/1998 | Bonadio et al. |
| 5,769,899 A | 6/1998 | Schwartz et al. |
| 5,770,229 A | 6/1998 | Tanihara et al. |
| 5,770,417 A | 6/1998 | Vacanti et al. |
| 5,782,835 A | 7/1998 | Hart et al. |
| 5,782,915 A | 7/1998 | Stone |
| 5,786,217 A | 7/1998 | Tubo et al. |
| 5,788,625 A | 8/1998 | Plouhar et al. |
| 5,800,537 A | 9/1998 | Bell |
| 5,814,084 A | 9/1998 | Grivas et al. |
| 5,824,055 A | 10/1998 | Spiridigliozzi et al. |
| 5,830,493 A | 11/1998 | Yokota et al. |
| 5,837,458 A | 11/1998 | Minshull et al. |
| 5,837,534 A | 11/1998 | Olson et al. |
| 5,842,477 A | 12/1998 | Naughton et al. |
| 5,846,931 A | 12/1998 | Hattersley et al. |
| 5,853,746 A | 12/1998 | Hunziker |
| 5,855,620 A | 1/1999 | Bishopric et al. |
| 5,859,208 A | 1/1999 | Fiddes et al. |
| 5,863,296 A | 1/1999 | Orton |
| 5,863,297 A | 1/1999 | Walter et al. |
| 5,863,792 A | 1/1999 | Tyndorf et al. |
| 5,868,415 A | 2/1999 | Villeneuve |
| 5,874,417 A | 2/1999 | Prestwich et al. |
| 5,878,444 A | 3/1999 | Lai |
| 5,878,452 A | 3/1999 | Athanasiou et al. |
| 5,881,733 A | 3/1999 | Stone |
| 5,888,219 A | 3/1999 | Bonutti |
| 5,893,888 A | 4/1999 | Bell |
| 5,899,936 A | 5/1999 | Goldstein |
| 5,899,939 A | 5/1999 | Boyce et al. |
| 5,902,741 A | 5/1999 | Purchio et al. |
| 5,904,716 A | 5/1999 | Gendler |
| 5,906,827 A | 5/1999 | Khouri et al. |
| 5,908,837 A | 6/1999 | Cohen et al. |
| 5,908,924 A | 6/1999 | Burdette et al. |
| 5,910,315 A | 6/1999 | Stevenson et al. |
| 5,916,285 A | 6/1999 | Hu |
| 5,916,557 A | 6/1999 | Berlowitz-Tarrant et al. |
| 5,922,028 A | 7/1999 | Plouhar et al. |
| 5,928,945 A | 7/1999 | Seliktar et al. |
| 5,942,496 A | 8/1999 | Bonadio et al. |
| 5,948,429 A | 9/1999 | Bell et al. |
| 5,949,252 A | 9/1999 | Taguchi |
| 5,952,191 A * | 9/1999 | Morozov ............ C12Q 1/24 435/288.4 |
| 5,955,438 A | 9/1999 | Pitaru et al. |
| 5,964,805 A | 10/1999 | Stone |
| 5,965,125 A | 10/1999 | Mineau-Hanschke |
| 5,972,385 A | 10/1999 | Liu et al. |
| 5,972,388 A | 10/1999 | McKay |
| 5,974,663 A | 11/1999 | Ikeda et al. |
| 5,976,524 A | 11/1999 | Hammerman |
| 5,989,269 A | 11/1999 | Vibe-Hansen et al. |
| 5,989,289 A | 11/1999 | Coates et al. |
| 5,989,866 A | 11/1999 | Deisher et al. |
| 5,998,170 A | 12/1999 | Arakawa et al. |
| 6,001,352 A | 12/1999 | Boyan et al. |
| 6,005,161 A | 12/1999 | Brekke et al. |
| 6,013,853 A | 1/2000 | Athanasiou et al. |
| 6,015,711 A | 1/2000 | Olson et al. |
| 6,017,348 A | 1/2000 | Hart et al. |
| 6,022,744 A | 2/2000 | Tetteroo et al. |
| 6,025,334 A | 2/2000 | Dupont et al. |
| 6,025,538 A | 2/2000 | Yaccarino, III |
| 6,027,742 A | 2/2000 | Lee et al. |
| 6,027,743 A | 2/2000 | Khouri et al. |
| 6,027,744 A | 2/2000 | Vacanti et al. |
| 6,030,635 A | 2/2000 | Gertzman et al. |
| 6,037,171 A | 3/2000 | Larsson |
| 6,039,762 A | 3/2000 | McKay |
| 6,042,610 A | 3/2000 | Li et al. |
| 6,056,777 A | 5/2000 | McDowell |
| 6,060,640 A | 5/2000 | Pauley et al. |
| 6,074,663 A | 6/2000 | Delmotte et al. |
| 6,080,194 A | 6/2000 | Pachence et al. |
| 6,090,996 A | 7/2000 | Li |
| 6,090,998 A | 7/2000 | Grooms et al. |
| 6,096,081 A | 8/2000 | Grivas et al. |
| 6,096,347 A | 8/2000 | Geddes et al. |
| 6,103,255 A | 8/2000 | Levene et al. |
| 6,110,209 A | 8/2000 | Stone |
| 6,110,482 A | 8/2000 | Khouri et al. |
| 6,110,746 A | 8/2000 | Cohen et al. |
| 6,118,043 A | 9/2000 | Nies et al. |
| 6,123,731 A | 9/2000 | Boyce et al. |
| 6,132,472 A | 10/2000 | Bonutti |
| 6,140,087 A | 10/2000 | Graham et al. |
| 6,143,293 A | 11/2000 | Weiss et al. |
| 6,146,385 A | 11/2000 | Torrie et al. |
| 6,150,163 A | 11/2000 | McPherson et al. |
| 6,156,068 A | 12/2000 | Walter et al. |
| 6,156,572 A | 12/2000 | Bellamkonda et al. |
| 6,159,179 A | 12/2000 | Simonson |
| 6,165,487 A | 12/2000 | Ashkar et al. |
| 6,171,610 B1 | 1/2001 | Vacanti et al. |
| 6,174,333 B1 | 1/2001 | Kadiyala et al. |
| 6,176,880 B1 | 1/2001 | Plouhar et al. |
| 6,180,605 B1 | 1/2001 | Chen et al. |
| 6,183,737 B1 | 2/2001 | Zaleske et al. |
| 6,189,537 B1 | 2/2001 | Wolfinbarger, Jr. |
| 6,193,647 B1 * | 2/2001 | Beebe ............... C12M 29/10 600/33 |
| 6,197,061 B1 | 3/2001 | Masuda et al. |
| 6,197,586 B1 | 3/2001 | Bhatnagar et al. |
| 6,200,347 B1 | 3/2001 | Anderson et al. |
| 6,201,165 B1 | 3/2001 | Grant et al. |
| 6,214,368 B1 | 4/2001 | Lee et al. |
| 6,221,854 B1 | 4/2001 | Radomsky |
| 6,231,607 B1 | 5/2001 | Ben-Bassat et al. |
| 6,231,879 B1 | 5/2001 | Li et al. |
| 6,235,316 B1 | 5/2001 | Adkisson |
| 6,242,247 B1 | 6/2001 | Rieser et al. |
| 6,261,143 B1 | 6/2001 | Schwartz et al. |
| 6,258,778 B1 | 7/2001 | Rodgers et al. |
| 6,261,586 B1 | 7/2001 | McKay |
| 6,267,786 B1 | 7/2001 | Stone |
| 6,270,528 B1 | 8/2001 | McKay |
| 6,274,090 B1 | 8/2001 | Coelho et al. |
| 6,274,663 B1 | 8/2001 | Hosokawa et al. |
| 6,274,712 B1 | 8/2001 | Springer et al. |
| 6,280,473 B1 | 8/2001 | Lemperle et al. |
| 6,281,195 B1 | 8/2001 | Rueger et al. |

(56) References Cited

U.S. PATENT DOCUMENTS

| | | |
|---|---|---|
| 6,283,980 B1 | 9/2001 | Vibe-Hansen et al. |
| 6,288,043 B1 | 9/2001 | Spiro et al. |
| 6,293,970 B1 | 9/2001 | Welfinbarger, Jr. et al. |
| 6,294,187 B1 | 9/2001 | Boyce et al. |
| 6,294,202 B1 | 9/2001 | Burns et al. |
| 6,294,359 B1 | 9/2001 | Fiddes et al. |
| 6,303,585 B1 | 10/2001 | Spire et al. |
| 6,305,379 B1 | 10/2001 | Wolfinbarger, Jr. |
| 6,306,169 B1 | 10/2001 | Lee et al. |
| 6,306,174 B1 | 10/2001 | Gie et al. |
| 6,306,424 B1 | 10/2001 | Vyakarnam et al. |
| 6,310,267 B1 | 10/2001 | Rapp |
| 6,312,725 B1 | 11/2001 | Wallace et al. |
| 6,315,992 B1 | 11/2001 | Noh et al. |
| 6,319,712 B1 | 11/2001 | Meenen et al. |
| 6,322,583 B1 | 11/2001 | Cummings et al. |
| 6,331,312 B1 | 12/2001 | Lee et al. |
| 6,333,029 B1 | 12/2001 | Vyakarnam et al. |
| 6,334,968 B1 | 1/2002 | Shapiro et al. |
| 6,337,198 B1 | 1/2002 | Levene et al. |
| 6,346,515 B1 | 2/2002 | Pitaru et al. |
| 6,352,558 B1 | 3/2002 | Spector |
| 6,352,971 B1 | 3/2002 | Deisher et al. |
| 6,361,565 B1 | 3/2002 | Bonutti |
| 6,371,958 B1 | 4/2002 | Overaker |
| 6,375,935 B1 | 4/2002 | Constantz |
| 6,376,244 B1 | 4/2002 | Atala |
| 6,378,527 B1 | 4/2002 | Hungerford et al. |
| 6,379,367 B1 | 4/2002 | Vibe-Hansen et al. |
| 6,379,385 B1 | 4/2002 | Kalas et al. |
| 6,383,221 B1 | 5/2002 | Scarborough et al. |
| 6,387,693 B2 | 5/2002 | Rieser et al. |
| 6,398,811 B1 | 6/2002 | McKay |
| 6,398,816 B1 | 6/2002 | Breitbart et al. |
| 6,398,972 B1 | 6/2002 | Blasetti et al. |
| 6,406,476 B1 | 6/2002 | Kirwan, Jr. et al. |
| 6,417,247 B1 | 7/2002 | Armstrong et al. |
| 6,425,918 B1 | 7/2002 | Shapiro et al. |
| 6,432,436 B1 | 8/2002 | Gertzman et al. |
| 6,432,713 B2 | 8/2002 | Takagi et al. |
| 6,437,018 B1 | 8/2002 | Gertzman et al. |
| 6,440,141 B1 | 8/2002 | Phiiippon |
| 6,440,427 B1 | 8/2002 | Wadstrom |
| 6,440,444 B2 | 8/2002 | Boyce et al. |
| 6,440,934 B1 | 8/2002 | Whitehouse |
| 6,443,988 B2 | 9/2002 | Felt et al. |
| 6,444,222 B1 | 9/2002 | Asculai et al. |
| 6,447,701 B1 | 9/2002 | Heschel et al. |
| 6,451,060 B2 | 9/2002 | Masuda et al. |
| 6,454,811 B1 | 9/2002 | Sherwood et al. |
| 6,458,144 B1 | 10/2002 | Morris et al. |
| 6,458,158 B1 | 10/2002 | Anderson et al. |
| 6,458,375 B1 | 10/2002 | Gertzman et al. |
| 6,468,314 B2 | 10/2002 | Schwartz et al. |
| 6,475,175 B1 | 11/2002 | Rivera et al. |
| 6,486,377 B2 | 11/2002 | Rapp |
| 6,488,033 B1 | 12/2002 | Cerundolo |
| 6,489,165 B2 | 12/2002 | Bhatnagar et al. |
| 6,489,455 B2 | 12/2002 | Chenchik et al. |
| 6,497,726 B1 | 12/2002 | Carter et al. |
| 6,503,277 B2 | 1/2003 | Bonutti |
| 6,504,079 B2 | 1/2003 | Tucker et al. |
| 6,511,511 B1 | 1/2003 | Slivka et al. |
| 6,511,958 B1 | 1/2003 | Atkinson et al. |
| 6,514,514 B1 | 2/2003 | Atkinson et al. |
| 6,517,872 B1 | 2/2003 | Yayon et al. |
| 6,520,964 B2 | 2/2003 | Tallarida et al. |
| 6,528,052 B1 | 3/2003 | Smith et al. |
| 6,530,956 B1 | 3/2003 | Mansmann |
| 6,533,821 B1 | 3/2003 | Lally |
| 6,534,084 B1 | 3/2003 | Vyakarnam et al. |
| 6,541,024 B1 | 4/2003 | Kadiyala et al. |
| 6,548,729 B1 | 4/2003 | Seelich et al. |
| 6,551,784 B2 | 4/2003 | Fodor et al. |
| 6,569,172 B2 | 5/2003 | Asculai et al. |
| 6,576,015 B2 | 6/2003 | Geistlich et al. |
| 6,576,265 B1 | 6/2003 | Spievack |
| 6,576,285 B1 | 6/2003 | Bader et al. |
| 6,579,538 B1 | 6/2003 | Spievack |
| 6,582,960 B1 | 6/2003 | Martin et al. |
| 6,591,581 B2 | 7/2003 | Schmieding |
| 6,592,598 B2 | 7/2003 | Vibe-Hansen et al. |
| 6,592,599 B2 | 7/2003 | Vibe-Hansen et al. |
| 6,599,300 B2 | 7/2003 | Vibe-Hansen et al. |
| 6,599,301 B2 | 7/2003 | Vibe-Hansen et al. |
| 6,599,515 B1 | 7/2003 | Delmotte |
| 6,607,879 B1 | 8/2003 | Cocks et al. |
| 6,623,963 B1 | 9/2003 | Muller et al. |
| 6,624,245 B2 | 9/2003 | Wallace et al. |
| 6,626,950 B2 | 9/2003 | Brown et al. |
| 6,630,000 B1 | 10/2003 | Bonutti |
| 6,630,457 B1 | 10/2003 | Aeschlimann et al. |
| 6,632,247 B2 | 10/2003 | Boyer, II et al. |
| 6,632,651 B1 | 10/2003 | Neve et al. |
| 6,645,727 B2 | 11/2003 | Thomas et al. |
| 6,645,764 B1 | 11/2003 | Adkisson |
| 6,652,592 B1 | 11/2003 | Grooms et al. |
| 6,652,593 B2 | 11/2003 | Boyer, II et al. |
| 6,652,872 B2 | 11/2003 | Neve et al. |
| 6,662,805 B2 | 12/2003 | Frondoza et al. |
| 6,666,892 B2 | 12/2003 | Hiles et al. |
| 6,673,286 B2 | 1/2004 | Shih et al. |
| 6,686,184 B1 | 2/2004 | Anderson et al. |
| 6,689,747 B2 | 2/2004 | Filvaroff et al. |
| 6,696,073 B2 | 2/2004 | Boyce et al. |
| 6,712,851 B1 | 3/2004 | Lemperle et al. |
| 6,727,224 B1 | 4/2004 | Zhang et al. |
| 6,730,314 B2 | 5/2004 | Jeschke et al. |
| 6,734,018 B2 | 5/2004 | Wolfinbarger, Jr. et al. |
| 6,737,072 B1 | 5/2004 | Angele et al. |
| 6,743,232 B2 | 6/2004 | Overaker et al. |
| 6,752,834 B2 | 6/2004 | Geistlich et al. |
| 6,753,311 B2 | 6/2004 | Fertala et al. |
| 6,761,739 B2 | 7/2004 | Shepard |
| 6,761,887 B1 | 7/2004 | Kavalkovich et al. |
| 6,764,517 B2 | 7/2004 | Yamamoto et al. |
| 6,767,369 B2 | 7/2004 | Boyer, II et al. |
| 6,773,723 B1 | 8/2004 | Spiro et al. |
| 6,776,800 B2 | 8/2004 | Boyer, II et al. |
| 6,783,712 B2 | 8/2004 | Slivka et al. |
| 6,790,454 B1 | 9/2004 | Abdul Malak et al. |
| 6,803,234 B2 | 10/2004 | Havenga et al. |
| 6,808,585 B2 | 10/2004 | Boyce et al. |
| 6,808,920 B2 * | 10/2004 | Goshoo ............... C12Q 1/6837 216/2 |
| 6,815,416 B2 | 11/2004 | Carney et al. |
| 6,838,440 B2 | 1/2005 | Stiles |
| 6,841,150 B2 | 1/2005 | Halvorsen et al. |
| 6,852,114 B2 | 2/2005 | Cerundolo |
| 6,852,125 B2 | 2/2005 | Simon et al. |
| 6,852,331 B2 | 2/2005 | Lai et al. |
| 6,855,167 B2 | 2/2005 | Shimp et al. |
| 6,855,169 B2 | 2/2005 | Boyer, II et al. |
| 6,855,189 B2 | 2/2005 | Ediinger |
| 6,858,042 B2 | 2/2005 | Nadler et al. |
| 6,866,668 B2 | 3/2005 | Giannetti et al. |
| 6,875,442 B2 | 4/2005 | Holy et al. |
| 6,884,428 B2 | 4/2005 | Binette et al. |
| 6,890,354 B2 | 5/2005 | Steiner et al. |
| 6,893,462 B2 | 5/2005 | Buskirk et al. |
| 6,893,466 B2 | 5/2005 | Trieu |
| 6,896,904 B2 | 5/2005 | Spiro et al. |
| 6,902,578 B1 | 6/2005 | Anderson et al. |
| 6,902,584 B2 | 6/2005 | Kwan et al. |
| 6,911,212 B2 | 6/2005 | Gertzman et al. |
| 6,932,977 B2 | 8/2005 | Heidaran et al. |
| 6,933,326 B1 | 8/2005 | Griffey et al. |
| 6,939,562 B2 | 9/2005 | Spiro et al. |
| 6,949,252 B2 | 9/2005 | Mizuno et al. |
| 6,962,814 B2 | 11/2005 | Mitchell et al. |
| 6,989,034 B2 | 1/2006 | Hammer et al. |
| 6,991,652 B2 | 1/2006 | Burg |
| 6,993,328 B1 | 1/2006 | Oommen |
| 6,995,013 B2 | 2/2006 | Connelly et al. |

(56) References Cited

U.S. PATENT DOCUMENTS

| | | | |
|---|---|---|---|
| 7,009,039 B2 | 3/2006 | Yayon et al. | |
| 7,018,416 B2 | 3/2006 | Hanson et al. | |
| 7,022,516 B2* | 4/2006 | Kanegasaki | B01L 3/5027 |
| | | | 435/288.5 |
| 7,025,916 B2 | 4/2006 | Bachrach | |
| 7,033,587 B2 | 4/2006 | Halvorsen et al. | |
| 7,041,641 B2 | 5/2006 | Rueger et al. | |
| 7,044,968 B1 | 5/2006 | Yaccarino, III et al. | |
| 7,045,141 B2 | 5/2006 | Merboth et al. | |
| 7,048,750 B2 | 5/2006 | Vibe-Hansen et al. | |
| 7,048,762 B1 | 5/2006 | Sander et al. | |
| 7,048,785 B2 | 5/2006 | Grooms et al. | |
| 7,067,123 B2 | 6/2006 | Gomes et al. | |
| 7,070,942 B2 | 7/2006 | Heidaran et al. | |
| 7,078,232 B2 | 7/2006 | Konkle et al. | |
| 7,087,082 B2 | 8/2006 | Paul et al. | |
| 7,108,721 B2 | 9/2006 | Huckle et al. | |
| RE39,321 E | 10/2006 | MacPhee et al. | |
| 7,115,146 B2 | 10/2006 | Boyer, II et al. | |
| 7,125,423 B2 | 10/2006 | Hazebrouck | |
| 7,125,569 B2 | 10/2006 | Nur et al. | |
| 7,132,110 B2 | 11/2006 | Kay et al. | |
| 7,137,989 B2 | 11/2006 | Asculai et al. | |
| 7,141,072 B2 | 11/2006 | Geistlich et al. | |
| 7,148,209 B2 | 12/2006 | Hoemann et al. | |
| 7,156,880 B2 | 1/2007 | Evans et al. | |
| 7,157,428 B2 | 1/2007 | Kusanagi et al. | |
| 7,163,563 B2 | 1/2007 | Schwartz et al. | |
| 7,166,133 B2 | 1/2007 | Evans et al. | |
| 7,169,610 B2 | 1/2007 | Brown | |
| 7,175,852 B2 | 2/2007 | Simmoteit et al. | |
| 7,179,299 B2 | 2/2007 | Edwards et al. | |
| 7,182,781 B1 | 2/2007 | Bianchi et al. | |
| 7,192,604 B2 | 3/2007 | Brown et al. | |
| 7,201,917 B2 | 4/2007 | Malaviya et al. | |
| 7,208,177 B2 | 4/2007 | Geistlich et al. | |
| 7,217,294 B2 | 5/2007 | Kusanagi et al. | |
| 7,220,558 B2 | 5/2007 | Luyten et al. | |
| 7,226,482 B2 | 6/2007 | Messerli et al. | |
| 7,241,316 B2 | 7/2007 | Evans et al. | |
| 7,252,987 B2 | 8/2007 | Bachalo et al. | |
| 7,264,634 B2 | 9/2007 | Schmieding | |
| 7,288,406 B2 | 10/2007 | Bogin et al. | |
| 7,291,189 B2 | 11/2007 | Hodorek | |
| 7,297,181 B2 | 11/2007 | Fell | |
| 7,299,805 B2 | 11/2007 | Bonutti | |
| 7,309,232 B2 | 12/2007 | Rutherford et al. | |
| 7,316,822 B2 | 1/2008 | Binette et al. | |
| 7,323,011 B2 | 1/2008 | Shepard et al. | |
| 7,323,445 B2 | 1/2008 | Zhang et al. | |
| 7,326,571 B2 | 2/2008 | Freyman | |
| 7,335,508 B2 | 2/2008 | Yayon et al. | |
| 7,338,492 B2 | 3/2008 | Singhatat et al. | |
| 7,338,524 B2 | 3/2008 | Fell et al. | |
| 7,358,284 B2 | 4/2008 | Griffey et al. | |
| 7,361,195 B2 | 4/2008 | Schwartz et al. | |
| 7,365,051 B2 | 4/2008 | Paulista et al. | |
| 7,371,400 B2 | 5/2008 | Barenstein et al. | |
| 7,452,677 B2 | 11/2008 | Lundgren-.ANG.kerlund | |
| 7,468,075 B2 | 12/2008 | Lang et al. | |
| 7,468,192 B2 | 12/2008 | Mizuno et al. | |
| 7,476,257 B2 | 1/2009 | Sah et al. | |
| 7,479,160 B2 | 1/2009 | Branch et al. | |
| 7,485,310 B2 | 2/2009 | Luyten et al. | |
| 7,488,348 B2 | 2/2009 | Truncale et al. | |
| 7,507,286 B2 | 3/2009 | Edidin et al. | |
| 7,513,910 B2 | 4/2009 | Buskirk et al. | |
| 7,524,513 B2 | 4/2009 | Hai-Quan et al. | |
| 7,531,000 B2 | 5/2009 | Hodorek | |
| 7,531,503 B2 | 5/2009 | Atala et al. | |
| 7,537,617 B2 | 5/2009 | Bindsell et al. | |
| 7,537,780 B2 | 5/2009 | Mizuno et al. | |
| 7,550,007 B2 | 6/2009 | Malinin | |
| 7,560,432 B2 | 7/2009 | Kusanagi et al. | |
| 7,563,455 B2 | 7/2009 | McKay | |
| 7,563,769 B2 | 7/2009 | Bogin et al. | |
| 7,595,082 B2 | 9/2009 | Pedrozo et al. | |
| 7,601,173 B2 | 10/2009 | Messerli et al. | |
| 7,608,113 B2 | 10/2009 | Boyer, II et al. | |
| 7,618,646 B2 | 11/2009 | Goerne et al. | |
| 7,621,963 B2 | 11/2009 | Simon et al. | |
| 7,622,438 B1 | 11/2009 | Lazarov et al. | |
| 7,622,562 B2 | 11/2009 | Thorne et al. | |
| 7,625,581 B2 | 12/2009 | Laredo et al. | |
| 7,628,851 B2 | 12/2009 | Armitage et al. | |
| 7,632,311 B2 | 12/2009 | Seedhom et al. | |
| 7,635,592 B2 | 12/2009 | West et al. | |
| 7,638,486 B2 | 12/2009 | Lazarov et al. | |
| 7,642,092 B2 | 1/2010 | Maor | |
| 7,648,700 B2 | 1/2010 | Vignery et al. | |
| 7,648,985 B2 | 1/2010 | Vignery et al. | |
| 7,658,768 B2 | 2/2010 | Miller et al. | |
| 7,662,184 B2 | 2/2010 | Edwards et al. | |
| 7,666,230 B2 | 2/2010 | Orban et al. | |
| 7,731,756 B2 | 6/2010 | Maspero et al. | |
| 7,763,272 B2 | 7/2010 | Offermann et al. | |
| 7,767,806 B2 | 8/2010 | Hirakura et al. | |
| 7,824,701 B2 | 11/2010 | Binette et al. | |
| 7,837,740 B2 | 11/2010 | Semler et al. | |
| 7,848,486 B2 | 12/2010 | Shea et al. | |
| 7,875,296 B2 | 1/2011 | Binette et al. | |
| 7,892,799 B2 | 2/2011 | Smith et al. | |
| RE42,208 E | 3/2011 | Truncale et al. | |
| 7,901,457 B2 | 3/2011 | Truncale et al. | |
| 7,901,461 B2 | 3/2011 | Harmon et al. | |
| 7,931,687 B2 | 4/2011 | Masuda et al. | |
| 8,029,992 B2 | 10/2011 | Rapko et al. | |
| 8,030,361 B2 | 10/2011 | Aso et al. | |
| 8,039,258 B2 | 10/2011 | Harris et al. | |
| 8,043,627 B2 | 10/2011 | Scharnweber et al. | |
| 8,062,655 B2 | 11/2011 | Johnson et al. | |
| 8,105,380 B2 | 1/2012 | Kharazi et al. | |
| RE43,208 E | 2/2012 | Yang et al. | |
| 8,110,007 B2 | 2/2012 | Borden | |
| 8,119,783 B2 | 2/2012 | Bogin et al. | |
| 8,147,882 B2 | 4/2012 | McKay | |
| 8,185,485 B2 | 5/2012 | Keith et al. | |
| 8,292,968 B2 | 10/2012 | Truncale et al. | |
| 8,420,858 B2 | 4/2013 | Hwang et al. | |
| 8,469,980 B2 | 6/2013 | Sengun et al. | |
| 8,507,261 B2 | 8/2013 | Ogihara et al. | |
| 8,685,107 B2 | 4/2014 | Claesson et al. | |
| 8,921,109 B2 | 12/2014 | Smith et al. | |
| 2001/0005592 A1 | 6/2001 | Bhatnagar et al. | |
| 2001/0006634 A1 | 7/2001 | Zaleske et al. | |
| 2001/0010023 A1 | 7/2001 | Schwartz et al. | |
| 2001/0011131 A1 | 8/2001 | Luyten et al. | |
| 2001/0011170 A1 | 8/2001 | Davison et al. | |
| 2001/0016646 A1 | 8/2001 | Rueger et al. | |
| 2001/0018619 A1 | 8/2001 | Enzerink et al. | |
| 2001/0020188 A1 | 9/2001 | Sander | |
| 2001/0021529 A1 | 9/2001 | Takagi | |
| 2001/0021875 A1 | 9/2001 | Enzerink et al. | |
| 2001/0031254 A1 | 10/2001 | Bianchi et al. | |
| 2001/0039457 A1 | 11/2001 | Boyer et al. | |
| 2001/0039458 A1 | 11/2001 | Boyer et al. | |
| 2001/0041941 A1 | 11/2001 | Boyer et al. | |
| 2001/0043940 A1 | 11/2001 | Boyce et al. | |
| 2001/0051834 A1 | 12/2001 | Frondoza et al. | |
| 2001/0055615 A1 | 12/2001 | Wallace et al. | |
| 2002/0009805 A1 | 1/2002 | Nevo et al. | |
| 2002/0016592 A1 | 2/2002 | Branch et al. | |
| 2002/0022884 A1 | 2/2002 | Mansmann | |
| 2002/0035401 A1 | 3/2002 | Boyce et al. | |
| 2002/0042373 A1 | 4/2002 | Carney et al. | |
| 2002/0045940 A1 | 4/2002 | Giannetti et al. | |
| 2002/0055783 A1 | 5/2002 | Tallarida et al. | |
| 2002/0062152 A1 | 5/2002 | Dauner et al. | |
| 2002/0072806 A1 | 6/2002 | Buskirk et al. | |
| 2002/0082220 A1 | 6/2002 | Hoemann et al. | |
| 2002/0082623 A1 | 6/2002 | Osther et al. | |
| 2002/0082704 A1 | 6/2002 | Cerundolo | |
| 2002/0099448 A1 | 7/2002 | Hiles et al. | |
| 2002/0106393 A1 | 8/2002 | Bianchi et al. | |

(56) References Cited

U.S. PATENT DOCUMENTS

| | | |
|---|---|---|
| 2002/0106625 A1 | 8/2002 | Hung et al. |
| 2002/0111695 A1 | 8/2002 | Kandel |
| 2002/0120274 A1 | 8/2002 | Overaker et al. |
| 2002/0138143 A1 | 9/2002 | Grooms et al. |
| 2002/0177224 A1 | 11/2002 | Madry et al. |
| 2002/0177859 A1 | 11/2002 | Monassevitch et al. |
| 2002/0192283 A1 | 12/2002 | Merboth et al. |
| 2003/0021827 A1 | 1/2003 | Malaviya et al. |
| 2003/0023316 A1 | 1/2003 | Brown et al. |
| 2003/0032981 A1 | 2/2003 | Pelo et al. |
| 2003/0033021 A1 | 2/2003 | Plouhar et al. |
| 2003/0033022 A1 | 2/2003 | Plouhar et al. |
| 2003/0036797 A1 | 2/2003 | Malaviya et al. |
| 2003/0036801 A1 | 2/2003 | Schwartz et al. |
| 2003/0039695 A1 | 2/2003 | Geistlich et al. |
| 2003/0040113 A1 | 2/2003 | Mizuno et al. |
| 2003/0044444 A1 | 3/2003 | Malaviya et al. |
| 2003/0049299 A1 | 3/2003 | Malaviya et al. |
| 2003/0050709 A1 | 3/2003 | Noth et al. |
| 2003/0055502 A1 | 3/2003 | Lang et al. |
| 2003/0078617 A1 | 4/2003 | Schwartz et al. |
| 2003/0095993 A1 | 5/2003 | Bentz et al. |
| 2003/0099620 A1 | 5/2003 | Zaleske et al. |
| 2003/0144743 A1 | 7/2003 | Edwards et al. |
| 2003/0198628 A1 | 10/2003 | Hammerman |
| 2003/0225355 A1 | 12/2003 | Butler |
| 2003/0229400 A1 | 12/2003 | Masuda et al. |
| 2003/0236573 A1 | 12/2003 | Evans et al. |
| 2004/0028717 A1 | 2/2004 | Sittinger et al. |
| 2004/0033212 A1 | 2/2004 | Thomson et al. |
| 2004/0039447 A1 | 2/2004 | Simon et al. |
| 2004/0044408 A1 | 3/2004 | Hungerford et al. |
| 2004/0062753 A1 | 4/2004 | Rezania et al. |
| 2004/0078090 A1 | 4/2004 | Binette et al. |
| 2004/0082084 A1 | 4/2004 | Reisner et al. |
| 2004/0102850 A1 | 5/2004 | Shepard |
| 2004/0107003 A1 | 6/2004 | Boyer et al. |
| 2004/0115172 A1 | 6/2004 | Bianchi et al. |
| 2004/0134502 A1 | 7/2004 | Mizuno et al. |
| 2004/0138748 A1 | 7/2004 | Boyer et al. |
| 2004/0143344 A1 | 7/2004 | Malaviya et al. |
| 2004/0151705 A1 | 8/2004 | Mizuno et al. |
| 2004/0166169 A1 | 8/2004 | Malaviya et al. |
| 2004/0170610 A1 | 9/2004 | Slavin et al. |
| 2004/0175826 A1 | 9/2004 | Maor |
| 2004/0192605 A1 | 9/2004 | Zhang et al. |
| 2004/0193154 A1 | 9/2004 | Leatherbury et al. |
| 2004/0193208 A1 | 9/2004 | Hazebrouck |
| 2004/0197307 A1 | 10/2004 | Rezania et al. |
| 2004/0197311 A1 | 10/2004 | Brekke et al. |
| 2004/0197373 A1 | 10/2004 | Gertzman et al. |
| 2004/0197375 A1 | 10/2004 | Rezania et al. |
| 2004/0214313 A1* | 10/2004 | Zhang .................. C12M 35/08 435/29 |
| 2004/0219182 A1 | 11/2004 | Gomes et al. |
| 2004/0220574 A1 | 11/2004 | Pelo et al. |
| 2004/0230303 A1 | 11/2004 | Gomes et al. |
| 2004/0234549 A1 | 11/2004 | Chiang et al. |
| 2004/0243242 A1 | 12/2004 | Sybert et al. |
| 2004/0267277 A1 | 12/2004 | Zannis et al. |
| 2005/0004672 A1 | 1/2005 | Pafford et al. |
| 2005/0027307 A1 | 2/2005 | Schwartz et al. |
| 2005/0038520 A1 | 2/2005 | Binette et al. |
| 2005/0042254 A1 | 2/2005 | Freyman et al. |
| 2005/0043814 A1 | 2/2005 | Kusanagi et al. |
| 2005/0064042 A1 | 3/2005 | Vunjak-Novakovic et al. |
| 2005/0074476 A1 | 4/2005 | Gendler et al. |
| 2005/0074481 A1 | 4/2005 | Brekke et al. |
| 2005/0089544 A1 | 4/2005 | Khouri et al. |
| 2005/0101957 A1 | 5/2005 | Buskirk et al. |
| 2005/0112761 A1 | 5/2005 | Halvorsen et al. |
| 2005/0125077 A1 | 6/2005 | Harmon et al. |
| 2005/0129668 A1 | 6/2005 | Giannetti et al. |
| 2005/0152882 A1 | 7/2005 | Kizer et al. |
| 2005/0159820 A1 | 7/2005 | Yoshikawa et al. |
| 2005/0159822 A1 | 7/2005 | Griffey et al. |
| 2005/0161857 A1 | 7/2005 | Coombes et al. |
| 2005/0191248 A1 | 9/2005 | Hunter et al. |
| 2005/0196480 A1 | 9/2005 | Malinin |
| 2005/0209705 A1 | 9/2005 | Niederauer et al. |
| 2005/0222687 A1 | 10/2005 | Vunjak-Novakovic et al. |
| 2005/0228498 A1 | 10/2005 | Andres |
| 2005/0240281 A1 | 10/2005 | Slivka et al. |
| 2005/0251288 A1 | 11/2005 | Truncate |
| 2005/0255458 A1 | 11/2005 | Polansky |
| 2005/0260612 A1 | 11/2005 | Padmini et al. |
| 2005/0261681 A9 | 11/2005 | Branch et al. |
| 2005/0261767 A1 | 11/2005 | Anderson et al. |
| 2005/0288796 A1 | 12/2005 | Awad et al. |
| 2006/0030948 A1 | 2/2006 | Manrique et al. |
| 2006/0060209 A1 | 3/2006 | Shepard |
| 2006/0099234 A1 | 5/2006 | Winkler |
| 2006/0105015 A1 | 5/2006 | Perla et al. |
| 2006/0111778 A1 | 5/2006 | Michalow |
| 2006/0141607 A1* | 6/2006 | Wikswo ............ B01L 3/502761 435/287.1 |
| 2006/0167483 A1 | 7/2006 | Asculai et al. |
| 2006/0178748 A1 | 8/2006 | Dinger et al. |
| 2006/0200186 A1 | 9/2006 | Hanson et al. |
| 2006/0204445 A1 | 9/2006 | Atala et al. |
| 2006/0210643 A1 | 9/2006 | Truncale et al. |
| 2006/0216323 A1 | 9/2006 | Knaack et al. |
| 2006/0216822 A1 | 9/2006 | Mizuno et al. |
| 2006/0235534 A1 | 10/2006 | Gertzman et al. |
| 2006/0247790 A1 | 11/2006 | McKay |
| 2006/0247791 A1 | 11/2006 | McKay et al. |
| 2006/0251631 A1 | 11/2006 | Adkisson et al. |
| 2006/0276907 A1 | 12/2006 | Boyer et al. |
| 2006/0286144 A1 | 12/2006 | Yang et al. |
| 2007/0009610 A1 | 1/2007 | Syring |
| 2007/0014867 A1 | 1/2007 | Kusanagi et al. |
| 2007/0026030 A1 | 2/2007 | Gill et al. |
| 2007/0036834 A1 | 2/2007 | Pauletti et al. |
| 2007/0041950 A1 | 2/2007 | Leatherbury et al. |
| 2007/0043376 A1 | 2/2007 | Leatherbury et al. |
| 2007/0055377 A1 | 3/2007 | Hanson et al. |
| 2007/0057175 A1 | 3/2007 | Mordehai et al. |
| 2007/0065943 A1 | 3/2007 | Smith et al. |
| 2007/0067032 A1 | 3/2007 | Felt et al. |
| 2007/0083266 A1 | 4/2007 | Lang |
| 2007/0093896 A1 | 4/2007 | Malinin |
| 2007/0093912 A1 | 4/2007 | Borden |
| 2007/0098759 A1 | 5/2007 | Malinin |
| 2007/0100450 A1 | 5/2007 | Hodorek |
| 2007/0113951 A1 | 5/2007 | Huang |
| 2007/0128155 A1 | 6/2007 | Seyedin et al. |
| 2007/0134291 A1 | 6/2007 | Ting et al. |
| 2007/0135917 A1 | 6/2007 | Malinin |
| 2007/0135918 A1 | 6/2007 | Malinin |
| 2007/0135928 A1 | 6/2007 | Malinin |
| 2007/0148242 A1 | 6/2007 | Vilei et al. |
| 2007/0162121 A1 | 7/2007 | Tarrant et al. |
| 2007/0168470 A1 | 7/2007 | Edwards et al. |
| 2007/0172506 A1 | 7/2007 | Nycz et al. |
| 2007/0178159 A1 | 8/2007 | Chen et al. |
| 2007/0179607 A1 | 8/2007 | Hodorek et al. |
| 2007/0185585 A1 | 8/2007 | Bracy et al. |
| 2007/0190030 A1 | 8/2007 | Pawliuk et al. |
| 2007/0202190 A1 | 8/2007 | Borden |
| 2007/0219497 A1 | 9/2007 | Johnson et al. |
| 2007/0276506 A1 | 11/2007 | Troxel |
| 2007/0299517 A1 | 12/2007 | Davisson et al. |
| 2007/0299519 A1 | 12/2007 | Schmieding |
| 2008/0015709 A1 | 1/2008 | Evans et al. |
| 2008/0027546 A1 | 1/2008 | Semler et al. |
| 2008/0031915 A1 | 2/2008 | Becerra Ratia et al. |
| 2008/0038314 A1 | 2/2008 | Hunziker |
| 2008/0039939 A1 | 2/2008 | Iwamoto et al. |
| 2008/0039954 A1 | 2/2008 | Long |
| 2008/0039955 A1 | 2/2008 | Hunziker |
| 2008/0051889 A1 | 2/2008 | Hodorek |
| 2008/0055210 A1 | 3/2008 | McKay |
| 2008/0064090 A1 | 3/2008 | Whittlinger |
| 2008/0077251 A1 | 3/2008 | Chen et al. |

(56) References Cited

U.S. PATENT DOCUMENTS

| | | | |
|---|---|---|---|
| 2008/0119947 | A1 | 5/2008 | Huckle et al. |
| 2008/0125883 | A1 | 5/2008 | McKay |
| 2008/0125888 | A1 | 5/2008 | Branemark et al. |
| 2008/0133008 | A1 | 6/2008 | Truncale et al. |
| 2008/0138414 | A1 | 6/2008 | Huckle et al. |
| 2008/0153157 | A1 | 6/2008 | Yao et al. |
| 2008/0154372 | A1 | 6/2008 | Peckham |
| 2008/0166329 | A1 | 7/2008 | Sung et al. |
| 2008/0167716 | A1 | 7/2008 | Schwartz et al. |
| 2008/0183300 | A1 | 7/2008 | Seedhom et al. |
| 2008/0220044 | A1 | 9/2008 | Semler et al. |
| 2008/0255676 | A1 | 10/2008 | Semler et al. |
| 2008/0260801 | A1 | 10/2008 | Ahlers et al. |
| 2008/0274157 | A1 | 11/2008 | Vunjak-Novakovic et al. |
| 2008/0287342 | A1 | 11/2008 | Yu et al. |
| 2008/0305145 | A1 | 12/2008 | Shelby et al. |
| 2008/0306408 | A1 | 12/2008 | Lo |
| 2009/0001267 | A1 | 1/2009 | Enyama et al. |
| 2009/0043389 | A1 | 2/2009 | Vunjak-Novakovic et al. |
| 2009/0069901 | A1 | 3/2009 | Truncale et al. |
| 2009/0069904 | A1 | 3/2009 | Picha |
| 2009/0076624 | A1 | 3/2009 | Rahaman et al. |
| 2009/0099661 | A1 | 4/2009 | Bhattacharya et al. |
| 2009/0112119 | A1 | 4/2009 | Kim |
| 2009/0117652 | A1 | 5/2009 | Luyten et al. |
| 2009/0131986 | A1 | 5/2009 | Lee et al. |
| 2009/0139045 | A1 | 6/2009 | Cannon et al. |
| 2009/0143867 | A1 | 6/2009 | Gage et al. |
| 2009/0148941 | A1 | 6/2009 | Florez et al. |
| 2009/0149893 | A1 | 6/2009 | Semler et al. |
| 2009/0210057 | A1 | 8/2009 | Liao et al. |
| 2009/0226523 | A1 | 9/2009 | Behnam et al. |
| 2009/0280179 | A1 | 11/2009 | Neumann et al. |
| 2009/0291112 | A1 | 11/2009 | Truncale et al. |
| 2009/0299475 | A1 | 12/2009 | Yamamoto et al. |
| 2009/0312805 | A1 | 12/2009 | Lang et al. |
| 2009/0312842 | A1 | 12/2009 | Bursac et al. |
| 2009/0319051 | A9 | 12/2009 | Nycz et al. |
| 2010/0015202 | A1 | 1/2010 | Semler et al. |
| 2010/0021521 | A1 | 1/2010 | Xu et al. |
| 2010/0036492 | A1 | 2/2010 | Hung et al. |
| 2010/0036503 | A1 | 2/2010 | Chen et al. |
| 2010/0241228 | A1 | 9/2010 | Syring et al. |
| 2010/0274362 | A1 | 10/2010 | Yayon et al. |
| 2010/0291181 | A1 | 11/2010 | Uhrich et al. |
| 2011/0053841 | A1 | 3/2011 | Yayon et al. |
| 2011/0070271 | A1 | 3/2011 | Truncale et al. |
| 2011/0196508 | A1 | 8/2011 | Truncale et al. |
| 2011/0224797 | A1 | 9/2011 | Semler et al. |
| 2011/0282372 | A1 | 11/2011 | Schowalter et al. |
| 2013/0273121 | A1 | 10/2013 | Mizuno et al. |

FOREIGN PATENT DOCUMENTS

| | | | |
|---|---|---|---|
| EP | 0337677 | A2 | 10/1989 |
| EP | 0517030 | A2 | 12/1992 |
| EP | 0522569 | A1 | 1/1993 |
| EP | 0608546 | A2 | 8/1994 |
| EP | 0620274 | A1 | 10/1994 |
| EP | 0674908 | A1 | 10/1995 |
| EP | 0677297 | A1 | 10/1995 |
| EP | 0739631 | A2 | 10/1996 |
| EP | 0784985 | A1 | 7/1997 |
| EP | 1127581 | A1 | 8/2001 |
| EP | 1181908 | A1 | 2/2002 |
| EP | 1208850 | A1 | 5/2002 |
| EP | 1234552 | A1 | 8/2002 |
| EP | 1234555 | A2 | 8/2002 |
| EP | 1264607 | A1 | 12/2002 |
| EP | 1384452 | A1 | 1/2004 |
| EP | 1452191 | A2 | 9/2004 |
| EP | 1537883 | A2 | 6/2005 |
| EP | 1561481 | A2 | 8/2005 |
| EP | 1625832 | A1 | 2/2006 |
| EP | 1719463 | A1 | 11/2006 |
| EP | 1719531 | A2 | 11/2006 |
| EP | 1719532 | A2 | 11/2006 |
| EP | 1923457 | A1 | 5/2008 |
| FR | 2657352 | A1 | 7/1991 |
| GB | 2102811 | A | 2/1983 |
| JP | 622744 | | 2/1994 |
| WO | 90/01342 | A1 | 2/1990 |
| WO | 90/11354 | A1 | 10/1990 |
| WO | 91/01140 | A1 | 2/1991 |
| WO | 91/09126 | A1 | 6/1991 |
| WO | 93/04169 | A1 | 3/1993 |
| WO | 93/16739 | A1 | 9/1993 |
| WO | 93/20218 | A1 | 10/1993 |
| WO | 94/03584 | A1 | 2/1994 |
| WO | 94/29442 | A2 | 12/1994 |
| WO | 95/25748 | A1 | 9/1995 |
| WO | 95/33502 | A1 | 12/1995 |
| WO | 96/01313 | A1 | 1/1996 |
| WO | 96/03159 | A1 | 2/1996 |
| WO | 96/15818 | A1 | 5/1996 |
| WO | 96/24310 | A1 | 8/1996 |
| WO | 96/40892 | A1 | 12/1996 |
| WO | 97/07668 | A1 | 3/1997 |
| WO | 97/07669 | A1 | 3/1997 |
| WO | 97/29715 | A1 | 8/1997 |
| WO | 97/40163 | A1 | 10/1997 |
| WO | 98/14222 | A1 | 4/1998 |
| WO | 98/41246 | A2 | 9/1998 |
| WO | 98/43686 | A1 | 10/1998 |
| WO | 98/44874 | A1 | 10/1998 |
| WO | 99/09914 | A1 | 3/1999 |
| WO | 99/11298 | A2 | 3/1999 |
| WO | 99/15209 | A2 | 4/1999 |
| WO | 99/21497 | A1 | 5/1999 |
| WO | 99/22747 | A1 | 5/1999 |
| WO | 99/48541 | A1 | 9/1999 |
| WO | 99/52572 | A1 | 10/1999 |
| WO | 99/56797 | A1 | 11/1999 |
| WO | 00/040177 | A1 | 7/2000 |
| WO | 00/44808 | A1 | 8/2000 |
| WO | 00/047114 | A1 | 8/2000 |
| WO | 00/47214 | A1 | 8/2000 |
| WO | 01/02030 | A2 | 1/2001 |
| WO | 01/07595 | A2 | 2/2001 |
| WO | 01/38357 | A2 | 5/2001 |
| WO | 01/39788 | A2 | 6/2001 |
| WO | 01/43667 | A1 | 6/2001 |
| WO | 01/46418 | A1 | 6/2001 |
| WO | 02/018546 | | 3/2002 |
| WO | 02/22779 | A2 | 3/2002 |
| WO | 02/36732 | A2 | 5/2002 |
| WO | 02/41877 | A1 | 5/2002 |
| WO | 02/058484 | A2 | 8/2002 |
| WO | 02/064180 | A1 | 8/2002 |
| WO | 02/077199 | A2 | 10/2002 |
| WO | 02/095019 | A1 | 11/2002 |
| WO | 03/007805 | A2 | 1/2003 |
| WO | 03/007873 | A2 | 1/2003 |
| WO | 03/007879 | A2 | 1/2003 |
| WO | 03/012053 | A2 | 2/2003 |
| WO | 03/035851 | A1 | 5/2003 |
| WO | 03/040113 | A1 | 5/2003 |
| WO | 03/049626 | A1 | 6/2003 |
| WO | 03/079885 | A2 | 10/2003 |
| WO | 03/087160 | A1 | 10/2003 |
| WO | 03/094835 | A2 | 11/2003 |
| WO | 2004/016276 | A1 | 2/2004 |
| WO | 2004/060404 | A1 | 7/2004 |
| WO | 2004/067704 | A2 | 8/2004 |
| WO | 2004/069298 | A1 | 8/2004 |
| WO | 2004/075940 | A1 | 9/2004 |
| WO | 2004/096983 | A2 | 11/2004 |
| WO | 2004/103224 | A1 | 12/2004 |
| WO | 2005/023321 | A2 | 3/2005 |
| WO | 2005/023906 | A1 | 3/2005 |
| WO | 2005/058207 | A1 | 6/2005 |
| WO | 2005/110278 | A2 | 11/2005 |
| WO | 2006/001046 | A1 | 1/2006 |
| WO | 2006/038287 | A1 | 4/2006 |

(56) References Cited

FOREIGN PATENT DOCUMENTS

| WO | 2006/042311 A2 | 4/2006 |
|---|---|---|
| WO | 2006/050213 A2 | 5/2006 |
| WO | 2006/113586 A2 | 10/2006 |
| WO | 2007/024238 A1 | 3/2007 |
| WO | 2007/035778 A2 | 3/2007 |
| WO | 2007/057175 A2 | 5/2007 |
| WO | 2008/013763 A2 | 1/2008 |
| WO | 2008/021127 A2 | 2/2008 |
| WO | 2008/038287 A2 | 4/2008 |
| WO | 2008/081463 A2 | 7/2008 |
| WO | 2008/106254 A2 | 9/2008 |
| WO | 2009/076164 A2 | 6/2009 |
| WO | 2009/111069 A1 | 9/2009 |
| WO | 2010/083051 A2 | 7/2010 |
| WO | 2013043072 A1 | 3/2013 |

OTHER PUBLICATIONS

OsteoSponge product information, Bacterin International Inc, May 2005.
Skolnick, J. et al., "From genes to protein structure and function: novel application of computational approaches in the genomic era" Trends BioTechnol., 2000, 18(1):34-39.
Doerks, T. et al., "Protein annotation: detectivework for protein prediction" Trends Genet., 1998, 14(6): 248-250.
Cook, J.L. et al., "Biocompatibility of three-dimensional chondrocyte grafts in large tibial defects of rabbits", Am J. Vet. Res., 2003, 64(1):12-20.
International Search Report and Written Opinion of the International Searching Authority dated Mar. 14, 2016 for International Application No. PCT/US2015/063161 (17 Pages).
Office Action dated Apr. 19, 2007 in connection with U.S. Appl. No. 11/151,270.
Office Action dated Aug. 19, 2009 In connection with U.S. Appl. No. 12/147,042.
Office Action dated Dec. 18, 2007 In connection with U.S. Appl. No. 11/081,103.
Office Action dated Feb. 20, 2007 tn connection with U.S. Appl. No. 10/960,960.
Office Action dated Feb. 6, 2007 in connection with U.S. Appl. No. 10/438,883.
Office Action dated Feb. 7, 2008 in connection with U.S. Appl. No. 10/815,778.
Office Action dated Jan. 14, 2010 in connection with U.S. Appl. No. 11/081,103.
Office Action dated Jul. 2, 2009 in connection with U.S. Appl. No. 10/815,778.
Office Action dated Jul. 22, 2009 in connection with U.S. Appl. No. 12/010,984.
Office Action dated Jul. 9, 2008 in connection with U.S. Appl. No. 11/151,270.
Office Action dated Jun. 3, 2009 in connection with U.S. Appl. No. 11/081,103.
Office Action dated Jun. 8, 2009 in connection with U.S. Appl. No. 11/481,955.
Office Action dated May 18, 2009 in connection with U.S. Appl. No. 11/657,042.
Office Action dated May 3, 2005 in connection with U.S. Appl. No. 10/438,883.
Office Action dated Nov. 12, 2008 in connection with U.S. Appl. No. 10/438,883.
Office Action dated Nov. 5, 2004 in connection with U.S. Appl. No. 10/438,883.
Office Action dated Oct. 5, 2005 in connection with U.S. Appl. No. 10/424,765.
Corpet, 1988, Multiple sequence alignment with hierarchical clustering, Nucleic Acids Res, 16(22):10881-90.
Coughlin et al., 1988, Acidic and Basic Fibroblast Growth Factors Stimulate Tyrosine Kinase Activity in Vivo, Journal of Biological Chemistry, 263(2):986-993.
Coulson et al., 1999, Collagen and a thermally reversible poloxamer deliver demineralized bone matrix (DBM) and biologically active proteins to sites of bone regeneration in: Portland Sons Symposium, Jeffrey O Hollinger: Proceedings from Portland Bone Symposium, Oregon Health Sciences University, US, 619-637.
Crameri et al., 1997, Molecular evolution of an arsenate detoxification pathway by DNA shuffling. Nature Biotech, 15:436-438.
Cuenco et, al., 2001, Cooperation of BCR-ABL and AML1/MDSU/EVI1 in blocking myeloid differentiation and rapid induction of an acute myelogenous leukemia, Oncogene, 20:8238-8248.
Dahlberg et, al., 1991, Demineralized Allogeneic Bone Matrix for Cartilage Repair, Journal of Orthopaedic Research, 9:11-19.
Danilenko et al., 1999, Recombinant rat fibroblast growth factor-16: structure and biological activity, Arch. Biochem. Blophys, 361:34-46.
De Jagereta et al., 2003, Simultaneous detection of 15 human cytokines in a singie sample of stimulated peripheral blood mononuclear cells, Clin & Diagn Lab Immunol, 10:133-139.
DeKoter et. al., 1998, EMBO 17:4456-4468.
Delezoide et. al., 1998, Spatio-temporal expression of FGFR 1, 2 and 3 genes during human embryo-fetal ossification, Mech Dev 77(1):19-30.
Dell'Accio et. al., 2001, Molecular markers predictive of the capacity of expanded human articular chondrocytes to form stable cartilage in vivo, Arthritis Rheum, 44(7):1608-19.
Dellow, et. al., 2001, Cardiovasc Res 50:3-6.
Deng et. al., 1996, Fibroblast Growth Factor Receptor 3 Is a Negative Regulator of Bone Growth, Cell 84:911-921.
Denissen et. al., 1994, Bone Miner, 25:123-134.
Denissen, et. al., 2009, J Periodontol, 71:279-86.
Diduch et. al., 2002, Joint Repair: Treatment Options far Articular Cartilage Injury Orthopedic Technology Review, 4:24-27.
Dinser et. al., 2001, Comparison of long-term transgene expression after non-viral and adenoviral gene transfer into primary articuiar chondrocytes, Histochem Cell Biol, 116(1):69-77.
Dionne et. al., 1990, Cloning and expression of two distinct high-affinity receptors cross-reacting with acidic and basic fibroblast growth factors, The EMBO Journal, 9(9):2685-2692.
Dreyfus et. al., 1995, Expression of the Evi-1 gene in myelodysplastic syndromes, Leukemia, 9:203-205.
Dvorakova et. al., 2001, Changes In The Expression Of FGFR3 In Patients With Chronic Myeloid Leukaemia Receiving Transplants Of Allogeneic Peripheral Blood Stem Cells, British Journal of Haematology, 113:832-835.
Eliopoulos et. al., 2002, Human cytidine deaminase as an ex vivo drug selectable marker in gene-modified primary bone marrow stromal cells, Gene Ther, 9:452-462.
Elroy-Stein et. al., 1989, Cap-independent translation of mRNA conferred by encephalomyocarditis virus 5' sequence improves the performance of the vaccinia virus/bacterophage T7 hybrid expression system, Proc. Natl. Acad. Sci., 86:6126-6130.
EP App No. 2004/0781499, Third party observation, mailed Jul. 30, 2014.
Eriksson et. al., 1991, Three-Dimensional structure of human basic fibroblast growth factor Proceedings of the National Academy of Science of USA, National Academy of Science, Washington, DC, US, 88:3441-3445.
Eriebacher et. al., 1995, Toward a Molecular Understanding of Skeletal Development, Cell, 80:371-378.
European Search Report and Opinion for EP1119081.17 dated Feb. 14, 2012, 10 pages.
Evans et. al., 2004, Osteoarthritis gene therapy Gene Ther, 11(4):379-89.
Extended European Search Report for European Patent Application No. 06814983.0, dated Apr. 19, 2012, 7 pages.
Ezzat et. al., 2002, Targeted Expression of a Human Pituitary Tumor-Derived Isoform of FGF Receptor-4 Recapitulates Pituitary Tumorigenesis, The Journal of Clinical Investigation, 109:69-78.
F Lincoln Avery, Anterior Cruciate Ligament (ACL) Graft Options, http://wwworthoassociatescom/ACL_graftshtm, Internet Article, The Sports Medicine Center, 1-15, Downloaded Jan. 9, 2007.

(56) References Cited

OTHER PUBLICATIONS

Feham et. al., 1998, Diversity Does Make a Difference: Fibroblast Growth Factor-Heparin Interactions, Current Opinion in Structural Biology, 8:578-586.
Feller et. al., 1984, Liposome encapsulation of retrovirus allows efficient superinfection of resistant cell lines, J Virol, 49(1):269-272.
Zhang et. al., 2004, Hyaline cartilage engineered by chondrocytes in pellet culture, histological., immunohistochemical and ultrastructural analysis in comparison with cartilage explants, J. Anat., 205(3):229-37.
Zhu et. al., 1995, GLU-96 of Basic Fibroblast Growth Factor Is Essential for High Affinity Receptor Binding Journal of Biological Chemistry, American, Society of Biochemical Biologists, Birmingham US, 270(37):21869-21874.
Zhu et. al., 1997, Analysis of high-affinity binding determinants in the receptor binding epitope of basic fibroblast growth factor, Protein Engineering, 10:417-421.
Messner et. al., 1996, The Long-term Prognosis for Severe Damage to Weight-bearing Cartilage in the Knee: A 14-year Clinical and Radiological Follow-up in 28 Young Athletes, Acta Orthopaedica Scandinavica, 67(2):165-168.
Mitani et. al., 1994, Generation of the AML1-EVI-1 fusion gene in the t(3;21)(q26;q22) causes blastic crisis in chronic myelocytic leukemia, EMBO J., 13(3):504-510.
Miyamoto et al., 1993, Molecular Cloning of Novel Cytokine cDNA Encoding the Ninth Member of the Fibroblast Growth Factor Family, Which Has a Unique Secretion Property, Molecular and Cellular Biology, 13:4251-4259.
Miyazaki, 2002, Random DNA fragmentation with endonuclease V: application to DNA shuffling, Nucleic Acids Research, 30(24):E139.
Mohammadi et. al., 2005, Structural Basis for Fibroblast Growth Factor Receptor Activation, Cytokine & Growth Factor Rev., 16:107-137.
Morishita et. al., 1992, Activation of the EVI1 gene expression in human acute myelogenous leukemias by translocations spanning 300-400 kilobases on chromosome 3q26, Proc. Natl. Acad. Sci. USA, 89:3937-3941.
Morishita et. al., 1992, Expression of the Evi-1 zinc finger gene in 32Dc13 myeloid cells blocks granulocytic differentiation in response to granulocyte colony-stimulating factor, Mol Cell Biol., 12:183-189.
Mucenski et. al., 1988, Identification of a Common Ecotropic Viral Integration Site, Evi-1, iii the DNA of AKXD Murine Myeloid Tumors, Molecular and Cellular Biology, 8:301-308.
Nakatake et. al., 2001, Identification of a Novel Fibroblast Growth Factor, FGF-22, Preferentially Expressed in the Inner Root Sheath of the Hair Follicle, Biochimica et. Biophysics Acta, 1517:460-463.
Naruo et. al., 1993, Novel Secretory Heparin-binding Factors from Human Glioma Cells (Glia-activating Factors) Involved in Glial Cell Growth, The Journal of Biological Chemistry, 268(4):2857-2884.
Needleman et. al., 1970, A General Method Applicable to the Search for Similarities in the Amino Acid Sequence of Two Proteins, J. Mol. Biol., 48:443-453.
Nehrer et. al., 1998, Chondrocyte-seeded Collagen Matrices Implanted in a Chondral Defect in a Canine Model, Biomaterials, 19:2313-2328.
Nettles et. al., 2004, in Situ Crosslinkable Hyaluranan for Articular Cartilage Repair, 50th Annual Meeting of the Orthopaedic Research Society, Paper No. 0202.
Nettles et. al., 2004, Photocrosslinkable Hyaluronan as a Scaffold for Articular Cartilage Repair, Annals of Biomedical Engineering, 32(3):391-397.
Neville-Webbe et al., 2002, The anti-tumour activity of bisphosphonates, Cancer Treatement Reviews 28(6):305-319.
Newman, 1998. Articular Cartilage Repair, American Journal of Sports Medicine, 26(2):309-324.

Ngo et. al., 1994, Computational complexity, protein structure prediction, and the Levirithal Paradox, In: The Protein Folding Problem and Tertiary Structure Prediction K Merz Jr and S Le Grand, Editors:433-506.
Nishimura et. al., 2000, Identification of a Novel FGF, FGF-21, Preferentially Expressed in the Liver, Biochimica et. Biophysica Acta, 1492:203-206.
Nixon et. al., 1999, Enhanced Repair of Extensive Articular Defects by Insulin-like Growth Factor-I-Laden Fibrin Composites, Journal of Orthopaedic Research, 17(4):475-487.
Non-final Office Action for U.S. Appl. No. 12/043,001, dated May 11, 2011.
Non-final Offce Action with regard to U.S. Appl. No. 12/381,072, dated Jan. 20, 2011.
O'Gorman et. al., 1991, Recombinase-mediated gene activation and site-specific integration in mammalian cells, Science, 251:1351-1355.
Obradovic et. al., 2001, Integration of Engineered Cartilage, Journal of Orthopaedic Research, 19:1089-1097.
Ochi et. al., 2001, Current Concepts in Tissue Engineering Technique for Repair of Cartilage Defect, Artificial Organs, 25(3):172-179.
Office Action for Canadian Patent Application No. 2,623,106, dated Jul. 10, 2012, 3 pages.
Office Action for Canadian Patent Application No. 2,623,106, dated Oct. 6, 2011, 4 pages.
Oh et. al., 2003, Signaling Mechanisms Leading to the Regulation of Differentiation and Apoptosis of Articular Chondrocytes by Insulin-like Growth Factor-1, Journal of Biological Chemistry, 278(38):36563-36571.
Okada-Ban et. al., 2000, Molecules in focus, Fibroblast Growth Factor-2, The International Journal of Biochemistry & Cell Biology, 32:263-267.
Olsen et. al., 2003, Fibroblast Growth Factor (FGF) Homologous Factors Share Structural but not Functional Homology with FGFs, J. Biol. Chem., 278(38):34226-34236.
Olsen et. al., 2004, Insights into the Molecular Basis for Fibroblast Growth Factor Receptor Autoinhibition and Ligand- Binding Promiscuity, Proc. Nati. Acad. Sci., 101:935-940.
Ornitz et. al., 1992, Ligand Specificity and Heparin Dependence of Fibroblast Growth Factor Receptors 1 and 3, The Journal of Biological Chemistry, 267(23):16305-16311.
Ornitz et. al., 1996, Receptor Specificity of the Fibroblast Growth Factor Family*, The Journal of Biological Chemistry, 271(25):15292-15297.
Ornitz et. al., 2001, Protein Family Review, Fibroblast Growth Factors Genome Biology, 2(3):30051-300512.
Ornitz, 2000, FGFs, heparan sulfate and FGFRs: complex interactions essential for development, Bioessays, 22(2):108-112.
Patent Examination Report No. 1 for Australian Patent Application No. 2006292224, dated Oct. 4, 2011, 3 pages.
Patent Examination Report No. 2 for Australian Patent Application No. 2006292224, dated Jul. 3, 2013, 4 pages.
Pearson et. al., 1988, Improved tools for biological sequence comparison, Proc. Natl. Acad. Sci. USA, 85(8):2444-2448.
Pei et. al., 2002, Bioreactors Mediate the Effectiveness of Tissue Engineering Scaffolds, The FASEB Journal., 16:1691-1694.
Pei et. al., 2002, Growth Factors for Sequential Cellular De- and Re-differentiation in Tissue Engineering, Biochemical and Biophysical Research Communications, 294:149-154.
Pellegrini et. al., 2000, Crystal Structure of Fibroblast Growth Factor Receptor Ectodomain Bound to Ligand and Heparin, Nature, 407:1029-1034.
Pereboeva et. al., 2003, Approaches to Utilize Mesenchymal Progenitor Cells as Cellular Vehicles, Stem Cells, 21:389-404.
Peretti et. al., 1998, Bonding of Cartilage Matrices with Cultured Chondrocytes: An Experiential Model, Journal of Orthopedic Research, 16(1):89-95.
Peretti et. al., 1999, Biomechanical Analysis of a Chondrocyte-Based Repair Model of Articular Cartilage, Tissue Engineering, 5(4):317-326.
Peretti et. al., 20130, Cell-based Tissue-Engineered Allogeneic Implant for Cartilage Repair, Tissue Engineering, 6(5):567-576.

(56) References Cited

OTHER PUBLICATIONS

Peretti et. al., 2001, A Biomedical Analysis of an Engineered Cell-Scaffold Implant for Cartilage Repair, Annals of Plastic Surgery, 46(5):533-537.
Peretti et. al., 2003, Cell-Based Bonding of Articular Cartilage: An Extended Study, Journal of Biomedical Materials Research, 64A:517-524.
Peretti et. al., 2007, In Vitro Bonding of Pre-seeded Chondrocyte, Sport Sciences for Health 2(1):29-33.
Peterson et. al., 2000, Two- to 9-year Outcome After Autologous Chondrocyte Transplantation of the Knee, Clinical Orthopaedics and Related Research, 374:212-234.
Peterson et. al., 2002, Autologous Chondrocyte Transplantation: Biomechanics and Long-term Durability, American Journal of Sports Medicine, 30(1):2-12.
Phillips, 2001, The challenge of gene therapy and DNA delivery, Journal of Pharmacy and Pharmacology, 53:1169/1174.
Piliai et. al., 2001, Polymers In Drug Delivery, Current Opinion Chemical Biology, 5:447-451.
Plotnikov et. al., 1999, Structural Basis for FGF Receptor Dimerization and Activation, Cell, 98:641-650.
Plotnikov et. al., 2000, Crystal Structures of Two FGF-FGFR Complexes Reveal the Deteminants of Ligand-Receptor Specificity, Cell 101:413-424.
Pollik et. al., 1995; J Oral Maxillofac Surg, 53(8):915-22.
Pouyani et. al., 1994, Functionalized Derivatives of Hyaluronic Acid Oligosaccharides: Drug Carriers and Novel Biomaterials, Bioconjugate Chem., 5:339-347.
Presta et. al., 1993, Subcellular Localization and Biological Activity of Mr 18,000 Basic Fibroblast Growth Factor: Site-Directed Mutagenesis of a Putative Nuclear Translocation Sequence, Growth Factors, 9:269-278.
Prestwich et. al., 1998, Controlled chemical modification of hyaluronic acid: synthesis, applications, and biodegradation of hydrazide derivatives, Journal of Controlled Release, 53:93-103.
Rabie et. al., 1996, Ultrastructural identification of cells involved in the healing of intramembranous and endochondral bones, Int J Oral Maxillofac Surg, 25(5):383-388.
Raisz, 1999, Physiology and Pathophysiology of Bone Remodeling, Clinical Chemistry, 45(8):1353-1358.
Richardson et. al., 1999, Repair of human articular cartilage after implantation of autologous chondrocytes, Journal of Bone and Joint Surgery [Br], 81-B:1064-1068.
Riggs et. al., 1987, Luciferase reporter gene cassettes for plant gene xpression studies, Nucleic Acid Res 15(19):8115.
Sahni et. al., 1999, FGF signalin inhibits chondrocyte proliferation and regulates bone development through the STAT-1 pathway Genes Dev., 13(11):1361-1386.
Santos-Ocampo et. al., 1996, Expression and Biological Activity of Mouse Fibroblast Growth Factor-9:, The Journal of Biological Chemistry, 271:1726-1731.
Schaefer et. al., 2002, Tissue Engineered Composites for the Repair of Large Osteochondral Defects, Arthritis & Rheumatism, 46(9):2524-2534.
Schlessinger et. al., 2000, Crystal Structure of a Ternary FGF-FGFR-Heparin Complex Reveals a Dual Role for Heparin in FGFR Binding and Dimerization, Molecular Cell, 6:743-750.
Schmal et. al., 2007, bFGF influences human articular chondrocyte differentiation, Cytotherapy, 9(2):184-193.
Schwartz et. al., 1991, A dominant positive and negative selectable gene for use mammalian cells, Proc. Natl. Acad. Sci. USA, 88(23):10416-20.
Schwarz et. al., 2000, Quantitative small-animal surrogate to evaluate drug efficacy in preventing wear debris-induced osteolysis, J Orthop Res, 18:849-55.
Schwindt et. al., 2009, Effects of FGF-2 and EGF removal on the differentiation of mouse neural precursor cells, An Acad Bras Cienc, 81(3):443-452.
Search Report Application No. PCT/IL2004/000088 dated Aug. 18, 2004.
Search Report conducted by the Australian Patent Office dated Mar. 14, 2008 regarding Singapore Patent Application No. 200607828-1.
Search Report conducted by the Danish Patent Office dated Jul. 15, 2005 regarding Singapore Patent Application No. 200406581-9.
Search Report for PCT/IL2007/001199, dated Sep. 16, 2008.
Search Report for PCT/US2008/073762 dated Dec. 22, 2008.
Search Report, PCT/IL07/01199, dated Sep. 16, 2008.
Seddon et. al., 1995, Engineering of Fibroblast Growth Factor Alteration of Receptor Binding Specificity, Biochemistry, 34:741-736.
Shaklee et. al., 1984, Hydrazinolysis of heparin and other glycosaminoglycans, Biochem. J., 217:187-197.
Sheo et. al., 2006, Effects of intramyocardial administration of slow-release basic fibroblast growth factor on angiogenesis and ventricular remodeling in a rat infarct model, Circ J, 70(4):471-477.
Shibata et. al., 2001, GM-CSF Regulates Alveolar Macrophage Differentiation and Innate Immunity in the Lung through PU.1, Immunity, 15(4):557-567.
Shu et. al, 2003, Attachment and spreading fibroblasts on an RGD peptide-modified injectable hyaluronan hydrogel, Wiley periodicals.
Shu et. al., 2004, Attachment and spreading of fibroblasts on an RGD peptide-modified injectable hyaluronan hydrogel, J Biomed, Mater Res 68A:365-375.
Sims et. al., 1998, Tissue Engineered Neocartilage Using Plasma Derived Polymer Substrates and Chondrocytes, Plastic & Recon Surg 101(6):1580-1585.
Skolnick et. al., 2000, From genes to protein structure and function: novel applications of computationai approaches in the genomic era, Trends BioTechnol, 18(1):34-39.
Sleeman et. al., 2001, Identification of a new fibrobiast growth factor receptor, FGFR5, Gene, 271(2): 171-182.
Smith et, al., 1996, In vitro stimulation of articular chondrocyte mRNA and extracellular matrix synthesis by hydrostatic pressure, Journal of Orthopaedic Research, John Wiley & Sons, Inc, 14(1):53-60.
Smith et. al., 1997, The challenges of genome sequence annotation or 'The devilis in the details, Nature Biotechnology, 15(12):1222-1223.
Soltes et al., 2003, Molecular characterization of two host-guest associating hyaluronan derivatives, Biomedical Chromatography, 17;376-384.
Song et. al., 2002, Construction of DNA-Shuffled and Incrementally Truncated Libraries by a Mutagenic and Unidirectional Reassembly Method: Changing from a Substrate Specificity of Phospholipase to That of Lipase, Appl. Environ. Microbiol., 68(12):6146-6151.
Spangenberg et. al., 2002, Histomorphometric Analysis of a Cell-Based Model of Cartilage Repair, Tissue Engineering, 8(5):839-46.
Springer et. al, 1994, Identification and Concerted Function of Two Receptor:Binding Surfaces on Basic Fibroblast Growth Factor Required for Mitogenesis, The Journal of Biological Chemistry, 269(43):26879-26884.
Stauber et. al., 2000, Structural interactions of fibroblast growth factor receptor with its ligands, PNAS, 97(1):49-54.
Stemmer et. al., 1994, DNA shuffling by random fragmentation and reassembly; in vitro recombination for molecular evolution, Proc. Natl. Acad. Sci, USA, 91(22):10747-10751.
Stone et. al., 2006, Articular Cartilage Paste Grafting to Full-Thickness Articular Cartilage Knee Joint Lesions: A 2- 12-Year Follow-up, Arthroscopy: The Journal of Arthroscopic and Related Surgery, 22(3):291-299.
Stone et. al., One-Step American Technique of Articular Cartilage Paste Grafting to Traumatic and Arthritic Defects in the Knee Joint (2-7 Years Follow-Up), downloaded from http:webarchive.Org/web/20041205005845/http://www.stoneclinic.com/onestepthm:published Dec. 5, 2004.
Sun et. al., 2001, Quantitative imaging of gene induction in living animals, Gene Therapy, 8:1572-1579.
Supplementary European Search Report for EP 03720833, with date of completed search as Apr. 11, 2008.
Supplementary European Search Report for EP 04706268, with date of completed search as Jan. 12, 2011.

(56) References Cited

OTHER PUBLICATIONS

Supplementary European Search Report for EP 05728956.3, with date of completed search as May 2, 2011.
Supplementary European Search Report for EP 07827173, with date of completed search as Oct. 30, 2009.
Supplementary European Search Report for EP02753826 dated Jul. 17, 2009, 2 pages.
Supplementary European Search Report for EP08768602 dated Oct. 22, 2012, 6 pages.
Supplementary European Search Report for EP087983003.3 dated Oct. 18, 2012, 6 pages.
Taylor et. el., 2002, In vitro osteoclast resorption of bone substitute biomaterials used for implant site augmentation: a pilot study, Int J Oral Maxillofac Implants, 17(3):321-30.
Thomson et. al., 1995, Fabrication of Biodegradable Polymer Scaffolds to Engineer Trabecular Bones, J Biomater Sci Polymer Edn, 7(1) :23-38.
Thuerauf et. al., 1997, Differential Effects of Protein Kinase C, Ras, and Raf-1 Kinase on the Induction of the Cardiac B-type Natriuretic Peptide Gene through a Critical Promoter-proximal M-CAT Element, J Biol Chem., 272:7464-7472.
Tokuriki et. al., 2009, Stability effects of mutations and protein evolvability, Current Opinion in Structural Biology, 19:596-604.
Tozer et. al., 2005, Tendon and ligament: Development, repair and disease, Birth Defects Research Part C, 75(3):226-236.
Tsumaki et. al., 1999, Role of CDMP-1 in Skeletal Morphogenesis: Promotion Mesenchymal Cell Recruitment and Chondrocyte Differentiation, J Cell Biol., 144(1):161-173.
Ui-Tei et, al., 2004, Guidelines for the selection highly effective siRNA sequences for mammlian and chick RNA interference, NAR 32(3):936-48.
U.S. Appl. No. 10/982,514, filed Nov. 5, 2004.
U.S. Appl. No. 10/982,514, Advisory Action dated Jun. 26, 2008.
U.S. Appl. No. 10/982,514, Advisory Action dated Oct. 23, 2008.
U.S. Appl. No. 10/982,514, Advisory Action dated Sep. 22, 2008.
U.S. Appl. No. 10/982,514, Final Office Action dated Feb. 1, 2008.
U.S. Appl. No. 10/982,514, Non-Final Office Action dated Jul. 17, 2007.
U.S. Appl. No. 10/982,514, Notice of Allowance dated Jan. 5, 2009.
U.S. Appl. No. 10/982,514, Requirement for Restriction/Election dated Apr. 4, 2007.
U.S. Appl. No. 12/416,435, Non-Final Office Action dated Mar. 22, 2011.
U.S. Appl. No. 12/416,435, Notice of Allowance dated Oct. 17, 2011.
U.S. Appl. No. 12/416,435, Restriction Requirement dated Dec. 10, 2010.
U.S. Appl. No. 13/347,823, Non-Final Office Action dated Nov. 21, 2012.
U.S. Appl. No. 13/347,823, Notice of Allowance dated Apr. 30, 2013.
U.S. Appl. No. 13/347,823, Restriction Requirement dated Jul. 23, 2012.
Vajo et. al., 2000, The Molecular and Genet.ic Basis of Fibroblast Growth Factor Receptor 3 Disorders: The Achondroplasia Family of Skeletal Dysplasias Muenke Craniosynostosis, and Crouzon Syndrome with Acanthosis Nigricans, Endocrine Rev 21(1):23-39.
Venkatesan et. al., 2004, Stimulation of proteoglycan synthesis by glucunosyltransferas-1 gene delivery: a strategy to promote cartilage repair, PNAS, 11(52):18087-92.
Verbruggen et. al., 1985, Repair Function in Organ Cultured Human Cartilage. Replacement of Enzymatically Removed Proteoglycans During Long term Organ Culture, The Journal of Rheumatology, 12(4).665-674.
Vidal et. al., 2005, Making sense of antisense, European Journal of Cancer, 41:2812-2818.
Vunjak-Novakovic et. al., 1999, Bioreactor Cultivation Conditions Modulate the Composition and Mechanical Properties of Tissue-Engineered Cartilage; Journal of Orthopaedic Research, 17:130-138.

Wade et. al., 1992, Codon usage tabulated from the GenBank genetic sequence data, Nucleic Acids Research, 20 (Supplernent):2111-2118.
Walsh et. al., 2003, Multiple tissue-specific promoters control expression of the murine tartrate-resistant acid phosphatase gene, Gene, 307:111-123.
Wang et. al., 1999, Overexpression of protein kinase C-? in the epidermis of transgenic mice results in striking alterations in phorbol ester-induced inflammation and COX-2, MIP-2 and TNF-alpha expression but not tumor promotion, Journal of Cell Science, 112:3497-3506.
Wells et. al., 1990, Additivity of Mutational Effects in Proteins Biochemistry, 29(37):8509.
Wilson et. al., 1977, Biological Properties of Polio Virus Encapsulated in Lipio Vesicles, Proc Natl Acad Sci, 74(8):3471-3475.
Winkler, 2013, Oligonucleotide conjugates for therapeutic applications, Ther Deliv., 4:791-809.
Wise et. al., 2002, American Surgeon, 68(6):553-end.
Wong et. al., 1995, Analysis of Putative Haparin-binding Domains of Fibroblast Growth Factor-1: Using Site-Directed Mutagenesis and Peptide Analogues, The Journal of Biological Chemistry, 270(43):25805-25811.
Woods at. al., 2005, Effectiveness of three extraction techniques in the development decellularized bone-anterior cruciate ligament-bone graft, Biomaterials, 26:7339-7349.
Written Opinion for PCT/IL2007/0011199, dated Sep. 16, 2008.
Written Opinion of the International Searching Authority Application No. PCT/IL2004/000088, dated Aug. 18, 2004.
Wu et. al., 2009, Multiple Synostoses Syndrome is Due to a Missense Mutation in Exon 2 of FGF9 Gene, The American Journal of Human Genetics, 85:53-63.
Yamashita et. al., 2000, Identification of a Novel Fibroblast Growth Factor, FGF-23, Preferentially Expressed in The Ventrolateral Thalamic Nucleus of the Brain, Biochemical and Biophysical Research Communications, 277:494-498.
Yang et. al., 1998, Improved fluorescence and dual color detection with enhanced blue and green variants of the green fluorescent protein, Journal of Biological Chemistry, 273:8212-6.
Yang et. al., 2000, Rac2 stimulates Akt activation affecting BAD/Bcl-XL expression while mediating survival and actin function in primary mast cells, Immunity, 12(5):557-568.
Yayon et, al., 1991, Cell Surface, Heparin-Like Molecules Are RequiredForBinding of Basic Fibroblast Growth Factor to Its High Affinity Receptor, Cell, 64:841-848.
Yayon et, al., 1993, Isolation of peptides that inhibit binding of basic fibroblast growthfactor to its receptor from a random phage-epitope library, Proc. Natl. Acad. Sci. USA, 90:10643-10647.
Yee et. al., 2000, Analysis of Fibroblast Growth Factor Receptor 3 S249C Mutation in Cervical Carcinoma, Journal of the National Cancer Institute, 92(22):1848-1849.
Young's Modulus, Entry on http://enwikipecliaorg accessed Oct, 27, 2005, 3 pages.
Zhang et. al., 1991, Three-dimensional structure of human basic fibroblast growth factor, a structural homology of interleukin 1 Beta, Proc. Natl. Acad. Sci. USA, 88(8):3446-3450.
Zhang et. al., 1997, Directed evolution of a fucosidase from a galactosidase by DNA shuffling anti screening, Proc. Natl. Acad. Sci. USA, 94:4504-4509.
Farndale et. al., 1982, A Direct Spectrophatometric Microassay for Sulfated Glycosaminoglycans in Carthage Cultures, Connective Tissue Research, 9(4):247-248.
Feczko et. al., 2003, Experimental Results of Donor Site Filling for Autologous Osteochondral Mosaicplasty, Arthroscopy: The Journal of Arthroscopic and Related Surgery, 19(7):755-761.
Final Office Action for U.S. Appl. No. 11/081,103, dated Aug. 11, 2010.
Fingl et. al., 1975, The Pharmacological Basis of Therapeutics, Ch 1:1.
Foldynova-Traritirkove et. al., 2012, Sixteen years and counting: the current understanding of fibroblast growth factor receptor 3 (FGFR3) signaling in skeletal dysplasias, Human Mutation, 33:29-41.
Fujibayashi et. al., 2001, J Long Term Eff Med implants:11:93-103.

(56) References Cited

OTHER PUBLICATIONS

Fujisato et. al., 1996, Effect of basic fibroblast growth factor on cartilage regeneration in chondrocyte-seeded collagen sponge scaffold, Biomaterials, 17:155-162.
Furth, et. al., 1994, Temporal control of genexpression in transgenic mice by a tetracycline-responsive promoter, Proc Natl Acad Sci USA, 91:9302-9306.
Gao et. al., 2002, Repair of Osteochondral Defect with Tissue-Engineered Two-Phase Composite Material Injectable Calcium Phosphate and Hyaluronan Sponge, Tissue Engineering Part A 8(5):827-837.
Gargiulo et. al., 2002, Phenotypic modulation of human articular chondrocytes by bistratene A, Eur Cell Mater, 3:9-18.
Garofalo et. al., 1999, Skeletal Dysplasia and Defective Chondrocyte Differentiation by targeted Overexpression of Fibroblast Growth Factor 9 in Transgenic Mice, Journal of Bone and Mineral Research, 14(11):1909-1915.
George et. al., 2006, Differentiation of Mesenchymal Stem Cells Into Osteoblasts on Honeycomb Collagen Scaffoids, Artificial Organs, 25(3):180-186.
George et. al., 2008, Biodegradable honeycomb collagen scaffold for dermal tissue engineering, J Biomed Mater Res 87A:1103-1111.
Gertzman et. al., 2001, A pilot study evaluating sodium hyaluronate as a carrier for freeze-dried demineralized bone powder, Cell and Tissue Banking, 2:87-94.
Gilbert et. at., 2006, Decellularization of Tissues and Organs, Biomaterials, 27(19):3675-3683.
Givol et. al., 1992, Complexity of FGF receptors: genetic basis for structural diversity and functional specificity, FASEB J., 6:3362-3369.
Glowacki et. al., 2001, Engineered Cartilage, Bone, Joints and Menisci-Potential for Temporomandibular Joint Reconstruction, Cells Tissues Organs, 189(3):302-308.
Goldberg et. al., 2005, Intra-articular hyaluronans: the treatment knee pain in osteoarthritis, Osteoarthritis Cartilage, 13(3):216-224.
Gooch et.al., 2001, IGF-I and Mechanical Environment Interact to Modulate Engineered Cartilage Development, Biochemical and Biophysical Research Communications, 286:909-915.
Gruber et, al., 2002, Platelets stimulate proliferation of bone cells: involvement of platelet.derived growth factor, microparticles and membranes, Clin Oral Implants Res., 13(5):529-535.
Guilak et. al., 2001, Functional tissue engineering: the role of biomechanics in articular cartilage repair. Clin Orthop Relat Res., (391 Suppl):S295-305.
Haisch et. al., 2000, Preparation of a pure autologous biodegradable fibrin matrix for tissue engineering, Cellular Engineering, Medical & Biological Engineering & Computing, 38:686-689.
Hayes et. al., 2002, Combining computational and experimental screening for rapid optimization ofprotein properties, Proc Nati Aced Sci U S A, 99:15926-31.
Hecht et. al., Structure of fibroblast growth factor 9 shows a symmetric dimer with unique receptor- and heparin-binding inerfaces, Acta Crysallogr D Biol Crystallogr, 57:378-384.
Herrera-Estrella et. al., 1983, Chimeric genes as dominant selectable markers in plant cells, EMBO J., 2(6):987-995.
Hidaka et. al., 2003, Acceleration of cartilage repair by genetically modified chondrocytes overexpressing bone morphogenetic protein-7, J Orthop Res, 21(4):573-83.
Hille et. al., 1990, Bleomycin resistance: a new dominant selectable marker for plant cell transformation, Plant Molecular Biology, 7:171-176.
Hoffman, 2002, Hydrogels for Biomedical Applications, Advanced Drug Delivery Reviews, 54(1):3-12.
Hromas et. al., 1993, Hematopoietic lineage-and stage-restricted expression the ETS oncogene family member PU.1, Blood 82:2998-3004.
http://www.stoneclinic.com/articularcartilagepastegrafting (Copyright 2009).
http://www.technobusiness-solutions.com/article-lyophilization1.html (published Feb. 12, 2002).
Hunziker, 1992, Articular Cartilage Structure in Humans and Experimental Animals, Articular Cartilage and Osteoarthritis, Raven Press, ed:183-199.
Hunziker, 1999, Articular cartilage repair: are the intrinsic biological constraints undermining this process insuperable?, Osteoarthritis and Cartilage 7(1):15-28.
Hunziker, 2001, Articular Cartilage Repair: Basic Science and Clinical Progress A Review of the Current Status and Prospects, Osteoarthritis and Cartilage, 10(6):432-463.
Ikeda et. al., 2000, Ex vivo gene delivery using an adenovirus vector in treatment for cartilage defects, J Rheumatol, 27(4):990-6.
lmamura et. al., 1990, Recovery of Mitogenic Activity of a Growth Factor Mutant with a Nuclear Translocation Sequence, Science, 249:1567-1570.
International Cartilage Repair Society, Cartilage Injury Evaluation Package, www.cartilage.org, 2000.
International Preliminary Examination Report for PCT/US02/09001 dated Oct. 30, 2004, (7 pages).
International Preliminary Report on Patentability Application No. PCT/IL2004/000088, dated Aug. 5, 2005.
International Preliminary Report on Patentability for International Patent Application No. PCT/US2004/010956, dated Nov. 18, 2005.
International Preliminary Report on Patentability for International Patent Application No. PCT/US2004/010957, dated Nov. 18, 2005.
International Preliminary Report on Patentability for International Patent Application No. PCT/US2005/008798 dated Nov. 1, 2006.
International Preliminary Report on Patentability for InternationalPatent Application No. PCT/US2005/030610, dated Feb. 26, 2008.
International Preliminary Report on Patentability for International Patent Application No. PCT/US2005/036878, dated Apr. 17, 2007.
International Preliminary Report on Patentability for International Patent Application No. PCT/US2008/051796, dated Jul. 28, 2009.
International Preliminary Report on Patentability for PCT/IL2001/00962, dated Oct. 18, 2006.
International Preliminary Report on Patentability for PCT/IL2007/001199 dated Mar. 21, 2009.
International Preliminary Report on Patentability for PCT/US2008/073762 dated Feb. 24, 2010, (6 pages).
International Preliminary Report on Patentability for PCT/US2009/001459, dated May 12, 2010.
International Search Report and Written Opinion for international Patent Application No. PCT/US2004/010956, dated Oct. 28, 2005.
Apr. 4, 2007 Requirement for Restriction/Election U.S. Appl. No. 10/982,514 (U.S. Pat. No. 7,563,769).
Jul. 17, 2007 Non-Finai Rejection U.S. Appl. No. 10/982,514 (U.S. Pat. No. 7,563,769).
Sep. 22, 2008 Advisory Action U.S. Appl. No. 10/982,514 (U.S. Pat. No. 7,563,769).
Advisory Action dated Oct. 23, 2008 for U.S. Appl. No. 10/982,514.
Advisory Action, dated Jun. 26, 2008, for U.S. Appl. No. 10/982,514.
Advisory Action, dated Sep. 22, 2008, for U.S. Appl. No. 10/982,514.
Final Office Action, dated Feb. 1, 2008, for U.S. Appl. No. 10/982,514.
Non-Final Office Action, dated Dec. 15, 2006, for U.S. Appl. No. 10/895,961.
Non-Final Office Action, dated Jul. 17, 2007, for U.S. Appl. No. 10/982,514.
Non-Final Office Action, dated Jun. 20, 2005, for U.S. Appl. No. 10/761,615.
A non-final Office Action dated Jan. 20, 2011 in connection with U.S. Appl. No. 12/381,072.
A non-final Office Action dated Mar. 1, 2011 in connection with U.S. Appl. No. 12/924,132.
Abbate et. al., 2001, Biotechniques 3 1:336-40.
Abraham et. al., 1996, Human Basic Fibroblast Growth Factor: Nucleotide Sequence and Genomic Organization, EMBO Journal., 5(10):2523-2528.
Agrawal et. al., 1991, Pharmacokinetics, Biodistribution, and Stabilityof Oligodeoxynucleotide Phosphorothioates in Mice, PNAS, 88:7595-7599.
Altschul et. al., 1990, Basic Local Alignment Search Tool, J Mol Biol 215:403-410.

(56) References Cited

OTHER PUBLICATIONS

Andres et. al., 2008, A Pro-Inflammatory Signature Mediates FGF2-nduced Angiogenesis, Journal of Cellular and Molecular Medicine, 13(8B):2083-2108.
U.S. Appl. No. 11/190,387, Advisory Action, dated Dec. 16, 2008 (16 pages).
U.S. Appl. No. 11/190,387, Advisory Action, dated Feb. 11, 2009 (7 pages).
U.S. Appl. No. 11/190,387, Advisory Action, dated Jan. 14, 2008 (3 pages).
U.S. Appl. No. 11/190,387, Advisory Action, dated Oct. 31. 2008 (15 pages).
U.S. Appl. No. 11/190,387, Final Rejection, dated Aug. 26, 2008 (12 pages).
U.S. Appl. No. 11/190,387, Final Rejection, dated Aug. 6, 2007 (18 pages).
U.S. Appl. No. 11/190,387, Non-Finai Rejection, dated Mar. 27, 2007 (21 pages).
U.S. Appl. No. 11/190,387, Non-Finai Rejection, dated Mar. 27, 2008 (11 pages).
U.S. Appl. No. 11/190,387, Requirement for Restriction/Eiection, dated Sep. 7, 2006 (7 pages).
U.S. Appl. No. 12/731,356, Non-Finai Rejection, dated Mar. 29, 2011 (14 pages).
U.S. Appl. No. 12/731,356, Requirement for Restriction/Eiection, dated Dec. 23, 2010 (6 pages).
Arai et. al., 2000, Gene delivery to human chondrocytes by an adeno associated virus vector J Rheumatol 27(4):979-82.
Arai et. al., 2004, Effect of adenovirus-mediated overexpression of bovine ADAMTS-4 and human ADAMTS-5 in primary bovine articuiar chondrocyte pellet culture system Osteoarthritis Cartilage, 8:599-613.
Arakawa et. al., 1993, Production and Characterization of an Analog of Acidic Fibroblast Growth Factor With Enhanced Stability and Biological Activity, Protein Engineering, 6(5):541-546.
Aston et ai., 1986, Repair of Articuiar Surfaces by Allografts of Articular and Growth-Plate Cartilage, Journal of Bone and Joint Surgery, 68-B(1):29-35.
Attwood, 2000, The Babel of bioinfonmatics, Science, 290:471-473.
Aviezer et. al., 1994, Differential Structural Requirements of Heparin and Heparan Sulfate Proteoglycans That Promote Binding of Basic Fibroblast Growth Factor To Its Receptor, The Journal of Biological Chemistry, 269(1):114-121.
Aviles et. al., 2003, Testing clinical therapeutic angiogenesis using basic fibrobiast growth factor (FGF-2), British Journal of Pharmacology, 140:637-646.
Bailly et. al., 2000, Uncoupling of Cell Proliferation and Differentiation Activities of Basic Fibroblast Growth Factor, FASEB Journal., 14:333-344.
Baird, 1994, Fibroblast growth factors: activities and significance of non-neurotrophin neurotrophic growth factors, Current Opinions in Neurobioiogy, 4:78-86.
Bange et. al., 2002, Cancer Progression and Tumor Cell Motility are Associated with the FGFR4 Arg 388 Allele, Cancer Research, 62:840-846.
Baragi et. al., 1995, Transplantation of transduced chondrocytes protects articular cartilage from interleukin 1-induced extracellular matrix degradation, J. Ciin. Invest. 96(5):2454-60.
Barralet et. al., 2000, Dissolution of dense carbonate apatite subcutaneously implanted in Wistar rats, J Biomed Mater Res, 49(2):176-82.
Bartholomew et. al., 1997, The Evi-1 proto-oncogene encodes a transcriptional repressor activity associated with transformation, Oncogene, 14:569-577.
Behr et. al., 2010, Fgf-9 is required for angiogenesis and osteogenesis in long bone repair, PNAS, 107(26):11853-11858.
Bellosta et. al., 2001, Identification of Receptor and Heparin Binding Sites in Fibrobiast Growth Factor 4 by Structure-Based Mutagenesis, Molecular and Cellular Biology 21(17):5946-5957.

Ben-Bassat et. al., 2000, in Biomateriais Engineering and Devices: Human Applications v2:155-169.
Berclaz et. al., 2002, regulates alveolar macrophage Fe?R-mediated phagocytosis and the IL-18/IFN?-mediated molecular connection between innate and adaptive immunity in the lung, Blood, 100:4193-4200.
Beynnon et. al., 2005, Treatment of Anterior Cruciate Ligament Injuries Part 2, The American Journal of Sports Medicine, 33(11):1751-1767.
Beynnon, et. al., 2005, Treatment of Anterior Cruciate Ligament Injuries Part 1, The American Journal of Sports Medicine, 33(10):1579-1602.
International Search Report and Written Opinion for International Patent Application No. PCT/US2004/010957, dated Nov. 1, 2004.
International Search Report and Written Opinion for International Patent Application No. PCT/US2005/008798, dated Jun. 19, 2006.
International Search Report and Written Opinion for International Patent Application No. PCT/US2005/030610, dated Apr. 7, 2006.
International Search Report and Written Opinion for International Patent Application No. PCT/US2005/036878, dated Sep. 21, 2006.
International Search Report and Written Opinion for International Patent Application No. PCT/US2008/085522, dated Jul. 6, 2009.
International Search Report and Written Opinion for International Patent Application No. PCT/US2008/001459, dated Jul. 6, 2009.
International Search Report and Written Opinion for PCT/US2008/007610 dated Oct. 8, 2008.
International Search Report and Written Opinion for PCT/US2010/000108 dated Aug. 24, 2010.
International Search Report for PCT/IL02/00589 dated Mar. 26, 2003.
International Search Report for PCT/US02/09001 dated Mar. 27, 2003, (2 pages).
Itoh et. al., 2001, A Honeycomb Collagen Carrier for Cell Culture as a Tissue Engineering Scaffold, Artificial Organs, 25(3):213-217.
Itokazu et. al., 1997, The Sustained Release of Antibiotic from Freeze-Dried Fibrin Antibiotic Compound and Efficacies in a Rat Model of Osteomyelitis, Infection, 25(6):359-363.
Iwamoto et. al., 1991, Reduction in Basic Fibroblast Growth Factor Receptor is Coupled with Terminal Differentiation of Chondrocytes, J Biol Chem 266(1):461-467.
Jackson et. al., 2001, Cartilage Substitute: Overview of Basic Science & Treatment Options, Journal of American Academy of Orthopaedic Surgeons, 9:37-52.
Jacobi et. al., 2011, MACI—a new era?, Arthroscopy, Rehabilitation, Therapy & Technology, http://www.smartjournal.com/content/3/1/10.
James et. al., 2000, Genetic manipulation of the rabbit heart via transgenesis, Circulation, 101:1715-1721.
Johnson et. al., 1993, Structural and Frunctional Diversity in the FGF Receptor Multigene Family, Advances in Cancer Research, 60:1-41.
Karlin et. al., 1990, Methods for assessing the statistical significance of molecular sequence features by using general scoring schemes, Proc. Natl. Acad. Sci. USA, 87:2264-2268.
Karlin et. al., 1993, Applications and statistics for multiple high-scoring segments in molecular sequences, Proc. Natl. Acad. Sci. USA, 90:5873-5877.
Kastrup et. al., 1997, X-rat Structure of the 154-Amino-Acid Form of Recombinant Human Basic Fibroblast Growth Factor Comparison with the Truncated 146-Amino-Acid Form, Acta Crystallographica, Section D53:160-168.
Kato et. al., 1990, Fibroblast Growth Factor is an Inhibitor of Chondrocyte Terminal Differentiation, Journal of Biological Chemistry, 265(10):5903-5909.
Keegan et. al., 1991, Isolation of an additional member of the fibroblast growth factor receptor family, FGFR-3, Proc. Natl. Acad. Sci. USA, 88:1095-1099.
Kiewitz et. al., 2009, Transcriptional regulation of S100A1 and exparession during mouse heart development, Biochim Biophys Acts, 1498:207-19.
Kim et. al., 2002, Alternative type I and I? turn conformations in the ?8/?9 ?-hairpin of human acidic fibroblast growth factor, Protein Science, 11(3):459-66.

(56) References Cited

OTHER PUBLICATIONS

Kirikoshi, 2000, Molecular Cloning and Characterization of Human FGF-20 on Chromosome 8p21.3-p22, Biochemical and Biophysical Research Communications, 274(2):337-343.

Kirker et. al., 2002, Glycosaminoglycan Hydrogel Films as Biointeractive Dressings for Wound Healing, Biomaterials, 23:3661-3671.

Kondo et. al., 2005, Effects of Administration of Exogenous Growth Factors on Biomechanical Properties of the Elongation-Type Anterior cruciate Ligament Infury With Partial Laceration, The American Journal of Sports Medicine, 33:188-196.

Kunkel, 1985, Rapid and efficient site-specific mutagenesis without phenotypic selection, Proc. Natl. Acad. Sci. USA, 82:488-492.

Kuroda et. al., 1999, Anabolic Effect of Amino terminally Truncated Fibroblast Growth Factor 4 (FGF4) on Bone, Bone, 25(4):431-437.

Kurokawa et. al., 2000, The Evi-1 oncoprotein inhibits c-Jun N-terminal kinase and prevents stress-induced cell death, EMBO J., 19:2958-2968.

Kuroyanagi et. al., 2001, Tissue-Engineered Product: Allogeneic Cultured Dermal Subsitute Composed of Spongy Collagen with Fibroblasts, Artificial Organs, 25(3):180-186.

Lakso et. al., 1992, Targeted oncogene activation by site-specific reombination in transgenic mice, Proc. Natl. Acad. Sci. USA, 89:6232-6236.

LaPointe et. al., 1996, Tissue-specific expression of the human brain natriuretic peptide gene in cardiac myocytes, Hypertension, 27:715-722.

Lev et. al., 1992, Dimerization and Activation of the Kit Receptor by Monovalent and Bivalent Binding of the Stem Cell Factor, The Journal of Biological Chemistry, 267, 15970-15977.

Li et. al., 2004, Synthesis and biological evaluation of a cross-linked hyaluronan-mitomycin C hydrogel, Biomacromolecules, 5(3):895-902.

Loeser et. al., 2005, Basic Fibroblast Growth Factor Inhibits the Anabolic Activity of Insulin-like Growth Factor 1 and Osteogenic Protein 1 in Adult Human Articular Chondrocytes, Arthritis & Rheumatism, 52(12):3910-3917.

Lorget et. al., 2012, Evaluation of the Therapeutic Potential of a CNP Analog in a Fgfr3 Mouse Model Recapituating Achondroplasis, Am J Hum Genet., 91(6):1108-1114.

Lu et. al., 2006, Minced Cartilage without Cell Culture Serves as an Effective Intraoperative Cell Source for Carilage Repair, Journal of Orthopaedic Research, 24:1261-1270.

Luo et. al., 1999, Synthesis and selective cytotoxicity of a hyaluronic acid-antitumor bioconjugate, Bioconjugate Chemicals, 10(5):755-763.

Madry et. al., 2003, Sustained transgene expression in cartilage defects in vivo after transplantation of articular chondrocytes modified by lipid-mediated gene transfer in a gel suspension delivery system, J Gene Med, 5(6):502-9.

Madry et. al., 2000, Efficient lipid-medicated gene transfer to articular chondrocytes, Gene Ther 7(4):286-91.

Madry et. al., 2002, Gene Transfer of a Human Insulin-like Growth Factor I cDNA Enhances Tissue Engineering of Cartilage, Human Gene Therapy, 13:1621-1630.

Madry et. al., 2003, Recombinant adeno-associated virus vectors efficiently and persistently transduce chondrocytes in normal and osteoarthritic human articular cartilage, Hum Gene Ther, 14(4):393-402.

Marian et. al., 1999, A transgenic rabbit model for human hypertrophic cardiomyopathy, J Clin Invest., 104:1683-1692.

Matsuda et. al., 1995, In Vivo Chrondrogenesis in Collagen Sponge Sandwiched by Perichondrium, J Biomater Sci Polymer Ed, 7(3):221-229.

Mazue et. al., 1991, Preclinical and Clinical Studies with Recombinant Human Basic Fibroblast Growth Factor, Annals New York Academy of Sciences:329-340.

Mbawuike et. al., 1989, a murine alveolar macrophage cell line: morphological, cytochemical, and functional characteristics, J Leukoc Biol., 46:119-127.

McKercher et. al., 1996, Targeted disruption of the PU.1 gene results in multiple hematopoietic abnormalities, EMBO J., 15:5647-5658.

McLeskey et. al., 1994, MDA-MB-134 Breast Carcinoma Cells Overexpress Fibroblast Growth Factor (FGF) Receptors and Are Growth-Inhibited by FGF Ligands, Cancer Research 54(2):523-530.

Messner et. al., 1996, Cartilage Repair: A Critical Review, Acta Orthopaedica Scandinavica, 67(5):523-529.

Bikfalvi et al., 1997, Biological Roles of Fibroblast Growth Factor-2, Endocrine Reviews, 18(1):26-45.

Blessing et. al., 1993, Transgenic mice as a model to study the role of TGF-beta-related molecules in hair follicles, Genes Dev, 7:204-215.

Bolander, 1992, Regulation of fracture repair by growth factors, Proc Soc Exp Biol Med., 200(2):165-170.

Bork et. al., 1996, Go hunting in sequence databases but watch out for the traps, Trends in Genetics 12(10):425-427.

Bork, 2000, Powers and pitfaiis in sequence analysis: The 70% hurdle. Genome Res 10(4):398-400.

Borok et. al., 2000, Differential regulation of rat aquaporin-5 promoter/enhancer activities in lung and salivary epithelial cells, J Biol Chem, 275:26507-14.

Bradford, 1976, A Rapid and Sensitive Method for the Quantitation of Micro-gram Quantities of Protein Utilizing the Principle of Protein-Dye Binding, Analytical Biochemistry, 72(1-2):248-254.

Bradley, 1987, Production and analysis of chimaeric mice. In Teratocarcinomas and Embryonic Stem Cells—A Practica Approach:113-152.

Breinan et. el., 1997, Effect of Cultured Autologous Chondrocytes on Repair of Chondral Defects in a Canine Model, Journal of Bone and Joint Surgery [Am], 79-A(10):1439-1451.

Breinan et al., 2001, Autologous Chondrocyte Implantation in a Canine Model: Change in Composition of Reparative Tissue with Time, Journal of Orthopaedic Research. 19:482-492.

Brenner, 1999, Errors in genome annotation, Trends in Genetics 15(4):132-133.

Brittberg et. al., 1994, Treatment of Deep Cartilage Defects in the Knee with Autologous Chondrocyte Transplantation, New England Journal of Medicine, 331(14):889-895.

Brittberg et. al., 1996, Rabbit Articular Cartilage Defects Treated with Autologous Cultured Chondrocytes, Clinical Orthopaedics and Related Research, 326:270-283.

Brittberg et. al., 2001, Autologous Chondrocytes Used for Articular Cartilage Repair: An Update, Clinical Orthopaedics and Related Research. 391 Suppl: S337-S348.

Brown et. al., 2005, Hyaluronic acid: a unique topical vehicle for the localized delivery of drugs to the skin, JEADV, 19(3):308-318.

Buckwalter et. al., 1998, Articular Cartiiage; Degeneration and Osteoarthritis, Repair, Regeneration, and Transplantation, AAOS Instructional Course Lectures, 47:487-504.

Bugbee, 2000, Fresh Osteochondral Allografting, Operative Techniques in Sports Medicine, 8(2):158-162.

Bujard, 1999, Controlling genes with tetracyclines, J Gene Med, 1:372-374.

Bulpitt et. al., 1999, New strategy for chemical modification of hyaluronic acid: Preparation of functionalized derivatives and their use in the formation of novel biocompatible hydrogels, J Biomed Mater Res, 47:152-169.

Burdette et. al., 1996, Cloning and expression of the gene encoding the Thermoanaerobacter ethanaiicus 39E secondary-alcohol dehydrogenase and biochemical characterization of the enzyme, Biochem J, 316:115-122.

Burger et. al., 2002, Fibroblast growth factor receptor-1 is expressed by endotheliai progenitor cells, Blood, 100(10):3527-35.

Bursac, 2002, Collagen Network Contributions to Structure-Function Relationships in Cartilaginous Tissues in Compression (Dissertation), Boston University College of Engineering.

Bystricky et. al., 2001, Nonbiodegradabie hyaluronan derivative prepared by reaction with a water-soluble carbodiimide Chem Paper, 1:49-52.

(56) References Cited

OTHER PUBLICATIONS

Cappellen et. al., 1999, Frequent Activating Mutations Of FGFR3 In Human Bladder And Cervix Carcinomas, Nature Genetics, 23:18-20.
Carr, 1988, Fibrin formed in plasma is composed of fibers more massive than those formed from purified fibrinogen, Thromb Haemost., 59(3):535-539.
Chalfie et. al., 1994, Green fluorescent protein as a marker for gene expression, Science 263:802-805.
Charron et. al., 1999, Cooperative Interaction between GATA-4 and GATA-6 Regulates Myocardial Gens Expression, Molecular & Cellular Biology 19(6):4355-4365.
Chellaiah et. al., 1994, Fibroblast Growth Factor Receptor (FGFR) 3. The Journal of Biological Chemistry 269(15):11620-11627.
Chen et. al., 1999, Repair of Articular Cartilage Defects: Part I Basic Science of Cartilage Healing, The American Journal of Orthopedics:31-33.
Chole et. al., 2001, JARO 2:65-71.
Chusho et. al., 2001, Dwarfism and Early Death in Mice Lacking C-Type Natriuretic Peptide, PNAS, 98(7):4016-4021.
Coffin et. al., 1997, Retroviruses Cold Spring Harber Laboratory Press:758-763.
Coiombier et. al., 1999, Cells Tissues Organs 164:131-140.
Communication pursuant to Article 94(3) EPC for European Patent Application No. 06814983.0, dated Sep. 23, 2013, 6 pages.
Cook et. al., 2003, Biocompatibiiity of three-dimensional chondrocyte grafts in large tibial defects of rabbits, Am J Vet. Res 64(1):12-20.
A Communication dated Oct. 9, 2007 in connection with U.S. Appl. No. 10/438,883.
A final Office Action dated Dec. 28, 2009 in connection with U.S. Appl. No. 11/657,042.
A final Office Action dated Jan. 7, 2010 in connection with U.S. Appl. No. 11/481,955.
A final Office Action dated Mar. 15, 2010 in connection with U.S. Appl. No. 10/815,778.
A final Office Action dated Nov. 13, 2008 in connection with U.S. Appl. No. 10/815,778.
A final Office Action dated Oct. 18, 2005 in connection with U.S. Appl. No. 10/438,883.
A final Office Action dated Sep. 19, 2008 in connection with U.S. Appl. No. 11/081,105.
A final Office Action dated Sep. 28, 2007 in connection with U.S. Appl. No. 10/960,960.
Advisory Action dated Dec. 27, 2007 in connection with U.S. Appl. No. 11/151,270.
Final Office Action dated Mar. 22, 2010 in connection with U.S. Appl. No. 12/010,984.
Final Office Action dated Oct. 9, 2007 In connection with U.S. Appl. No. 11/151,270.
Non-Finai Office Action dated Apr. 12, 2010 in connection with U.S. Appl. No. 12/191,490.
Non-Final Office Action dated Apr. 15, 2010 in connection with U.S. Appl. No. 11/657,042.
Non-Final Office Action dated Apr. 15, 2010 in connection with U.S. Appl. No. 12/079,629.
Non-Final Office Action dated Apr. 26, 2010 in connection with U.S. Appl. No. 12/147,042.

\* cited by examiner

CELL AND TISSUE CULTURE CONTAINER

CROSS-REFERENCE TO RELATED APPLICATIONS

This application is a divisional of U.S. patent application Ser. No. 14/558,080, filed Dec. 2, 2014, which is herein incorporated by reference in its entirety.

FIELD OF THE INVENTION

The invention generally relates to cell and tissue culture devices.

BACKGROUND

While certain tissues in the human body, such as skin, are capable of self-repair (e.g., wound healing), there are many tissues that are not. For example, articular cartilage has no innate ability to repair itself, rendering any damage thereto permanent. Articular cartilage lines opposing bone surfaces in diarthrodial joints and provides a smooth, lubricated surface for articulation. Accordingly, defects in articular cartilage tend to expand and worsen over time. Damage to the articular cartilage in joints such as the knee can lead to debilitating pain.

Typical treatment choices, depending on lesion and symptom severity, are rest and other conservative treatments, minor arthroscopic surgery to clean up and smooth the surface of the damaged cartilage area, and other surgical procedures such as microfracture, drilling, and abrasion. All of these may provide symptomatic relief, but the benefit is usually only temporary, especially if the person's pre-injury activity level is maintained. For example, severe and chronic forms of knee joint cartilage damage can lead to greater deterioration of the joint cartilage and may eventually lead to a total knee joint replacement. Approximately 200,000 total knee replacement operations are performed annually. The artificial joint generally lasts only 10 to 15 years and the operation is, therefore, typically not recommended for people under the age of fifty.

An alternative treatment is implantation of cultured neo-cartilage (i.e., immature hyaline cartilage) which can be grown in-vitro to a desired size and shape on a 3D scaffold from chondrocyte cells biopsied from the patient (autologous) or from another individual (heterologous). Examples of this process are described, for example, in U.S. Pat. Nos. 6,949,252; 7,537,780; 7,468,192; 7,217,294; and U.S. patent application Ser. No. 14/208,931. An exemplary method for 3D culture of neo-cartilage is shown in FIG. 8 and includes the steps of isolating chondrocyte cells from a biopsy, 2D growth of cells, seeding of a 3D scaffold, and two culturing steps. The first culturing step takes place under controlled pressure, oxygenation, and perfusion conditions to mimic the joint environment while the second culturing step is a 3D static culture.

Along with the neo-cartilage for implantation, multiple other surrogate tissues are simultaneously cultured in the same vessel in order to permit pre-implantation testing and verification procedures without damaging the neo-cartilage to be implanted.

Current culture containers include narrow opening flask-type containers with a sealing cap with a gas-permeable filter membrane but the 3D static culture procedure presents multiple challenges which are unmet by current culture containers. For example, the surrogates and the neo-cartilage to be implanted need to be cultured in the same conditions in a common fluid to enable validation through surrogate testing. However, in current containers, the surrogates and neo-cartilage can grow into one another as they mature and then require separation which can damage the cells and scaffolds. Another problem stems from the fact that the tissues must be submerged in fluid during the 3D static culture but the buoyancy of the cultures varies during tissue growth. The 3D static culture process takes 2 weeks and requires incubation throughout the process, taking up space in expensive incubators and limiting production efficiency and capacity using bulky flask-type containers. Additionally, the surrogates and the neo-cartilage to be implanted must be transferred from one container to another during the 2 week process and then must be removed from the container before final packaging for distribution and implantation. Manipulation of the neo-cartilage to be implanted and the surrogates through the narrow opening of the current culture containers is difficult and can cause damage to the cells. These challenges are not unique to 3D static culturing of neo-cartilage and apply to a variety of cell and tissue culturing procedures.

SUMMARY

The invention relates to containers for cell and tissue culturing with multiple compartments in fluid communication with each other to provide a common culture environment in each of the compartments while maintaining physical separation of cells and tissue therein. Culture containers of the invention can be used to simultaneously culture one or more surrogate tissues alongside and under the same conditions as a tissue to be implanted, thereby enabling destructive testing and verification procedures to be carried out without harming the tissue to be implanted. Each compartment may contain the same type of tissue or different tissue types in order to investigate interactions between different tissue types. In some instances multiple tissue types may be cultured in a single compartment. The containers of the present invention provide containers for culturing these tissues in a common environment and fluid while preventing the surrogate tissues and the tissue for implantation from adhering or growing onto the container or each other and potentially damaging the tissue for implantation. Containers of the invention may provide sealing lids with gas permeable membranes to allow for gas exchange between the interior and exterior environments of the container while maintaining a sterile internal environment. The culture containers and lids may be configured to minimize height while maintaining adequate interior volume and maximizing incubator efficiency and space. Containers of the invention may also provide multiple compartments in fluid communication yet capable of restricting movement of and various sizes of sometimes buoyant tissue cultures and other materials. Additionally, culture containers of the invention may provide a large opening with easy, lid-off access to each compartment and any tissue or other materials therein. The several features of the containers of invention provide a more efficient platform for culturing and verifying cells and tissues for implantation while minimizing the potential for damage to the implantable tissue.

Culture containers of the invention may comprise a bottom wall and at least one side wall coupled thereto. Side walls may form right angles with the bottom wall or may taper out to provide a large opening with easy access to the compartments therein. Culture containers can be a cylinder, a cuboid, a triangular prism, a pentagonal prism, an octagonal prism or a variety of other 3 dimensional shapes.

Containers of the invention may include one or more interior walls which can divide the interior volume of the container into two or more compartments. A container may have 11 or more compartments or as few as two. The compartments may be of the same size or a variety of sizes. In some instances a larger compartment may be configured to contain cultured tissue for implantation while several smaller compartments may be sized to contain surrogates for testing.

In certain aspects, the container may comprise multiple components such as a first unit comprising a bottom wall and at least one side wall and a second unit comprising one or more of the interior walls or partition so that the partition may be removed from the container providing a single compartment or inserted into the container to provide multiple compartments therein. In certain instances, a single first component comprising the one or more side walls and the bottom wall may be compatible with multiple different second components comprising interior walls in various configurations so that, by interchanging second components, the number of compartments may be varied.

In order to achieve fluid communication between the compartments of the container, the interior walls may have openings including pores, slits, or gaps between an interior wall and a side wall, the bottom wall, or the lid. The openings may be dimensioned so as to allow fluid to pass between the compartments of the container without allowing cells, tissues, or 3D scaffolds to pass therebetween. Screens or filters may be used to cover openings in order to help restrict passage of cells, tissues, or 3D scaffolds therethrough.

Devices of the invention may include a lid configured to detachably couple to the top edge of the one or more side walls in order to enclose the container. The lid can generally correspond in shape and size to the opening formed by the top edge of the one or more side walls. The lid may be configured to form an air or water-tight seal when detachably coupled to the container, may include a gasket to aid in sealing, and may be secured via complementary threads, interlocking tabs, or other means. Preferably, the lid and the container may be detachably coupled without the use of tools in order to promote sterility and relatively easily in order to avoid excessive motion of the contained fluid and disruption of the cultured materials.

The lid may comprise a vent and/or a gas permeable membrane of a size and shape configured to allow gas to pass into and out of a sealed container while restricting undesirable particles such as bacteria, endotoxins, and other contaminants. The lid may be configured so that, when detachably coupled to the container, the only avenue for gas exchange between the interior and exterior of the container is through the filter. A filter may also be located on a side wall of the container.

Containers of the invention may be sized so that containers may contain an adequate volume of fluid (e.g., 500 mL) while maintaining sufficient space between the fluid and the lid to avoid contact during movement of the container and so that multiple containers can fit on a standard incubator tray to maximize space efficiency during the incubation process.

The lid, the container, or components thereof may comprise a variety of materials including, for example, polypropylene, high-density polyethylene, polystyrene, styrene-acrylonitrile (SAN), polycarbonatestyrene-maleic anhydride (SMA), cyclic olefin copolymers (COC), acrylic, acrylic-polyvinyl chloride alloys, polypropylene copolymers, polysulfone, polymethylpentene, or cellulosic. The lid, the container, or components thereof may comprise a substantially transparent material to allow visual inspection of the container's contents from outside of the container. Containers and lids may be configured as single-use disposables or may be configured for repeated use and sterilization.

In some aspects, the interior surface of the bottom wall, the interior surface of the one or more side walls, and/or the surfaces of the one or more interior walls may be smooth; textured with ridges, valleys, pores, or dimples; and/or treated with an agent to deter adherence of cultured cells or tissues and/or the facilitate retrieval from the container by scooping under the cultured tissue with a retrieval tool.

DETAILED DESCRIPTION

The invention relates to culture containers comprising multiple compartments configured to be in fluid communication with each other while maintaining physical separation of cell or tissues being cultured therein. Cells and tissues are cultured on 3D scaffolds to form tissues of a desired shape and size. If a tissue is being cultured for implantation, it is advantageous to simultaneously culture one or more surrogate tissues under the same conditions to enable destructive testing and verification procedures to be carried out without harming the tissue to be implanted. The containers of the present invention provide containers for culturing these tissues in a common environment and fluid while preventing the surrogate tissues and the tissue for implantation from adhering or growing onto the container or each other and potentially damaging the tissue for implantation. In various embodiments, each compartment in a container may contain the same type of tissue or different tissue types in order to investigate effects of different types of tissue on each other in a shared culture environment. In certain instances multiple tissue types may be cultured in a single compartment to investigate physical interactions between the tissues. Culture containers of the invention may be used to culture a variety of cells and tissues including chondrocytes, mesenchymal stem cells, fibroblasts, osteocytes, osteoblasts, synoviocytes, induced pluripotent stem cells (iPSC), embryonic stem cells (ESC), lymphocytes, adipocytes, myofibroblasts, hepatocytes, islet cells, monocytes, endometrial regenerative cells, or cancer stem cells. Applications for these containers include the culturing of neo-cartilage from chondrocytes for repair of articular cartilage defects.

Figure 1:
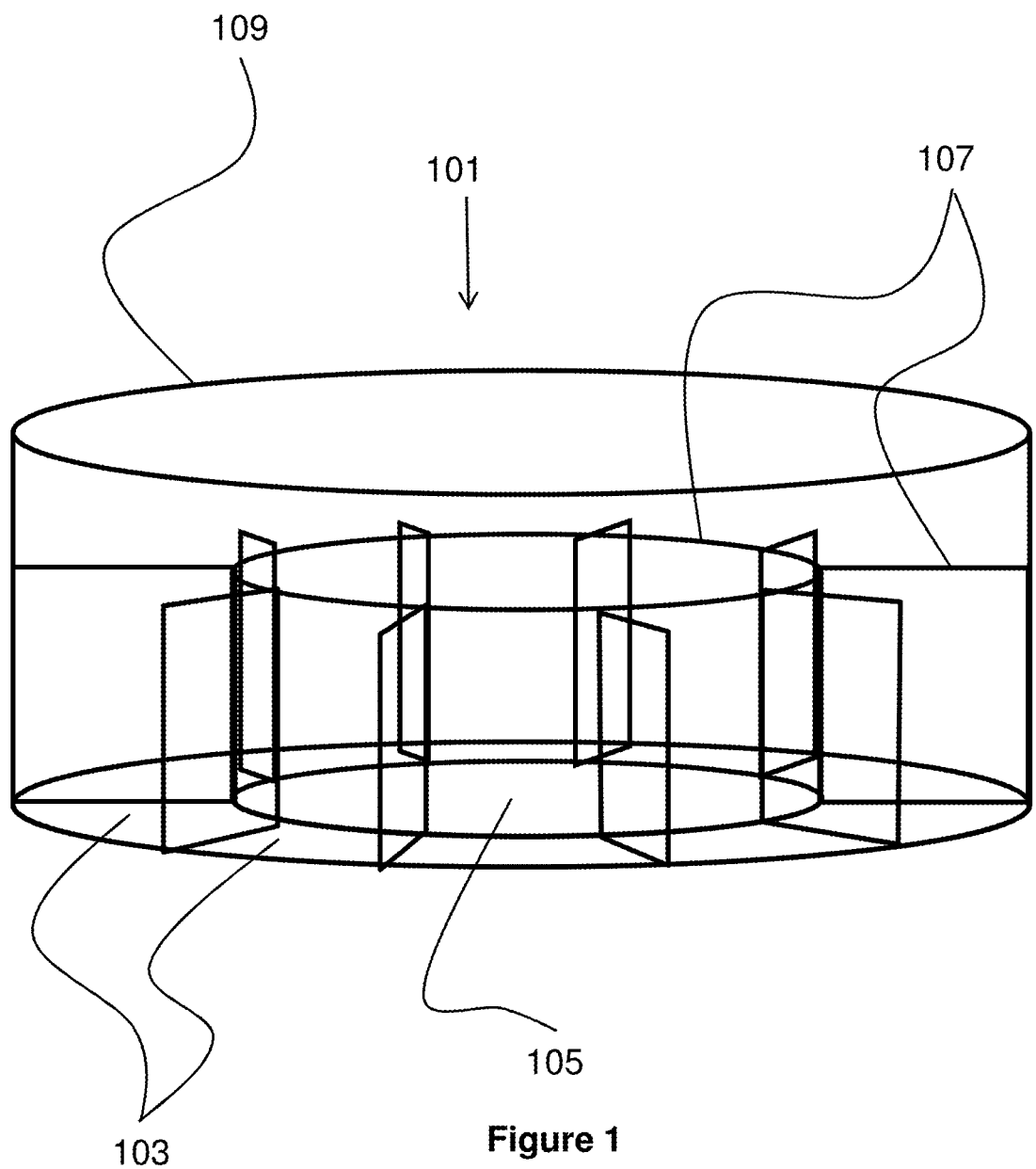
FIG. 1 shows a side view of an exemplary embodiment of a circular multi-compartment culture container of the invention.
Figure 3:
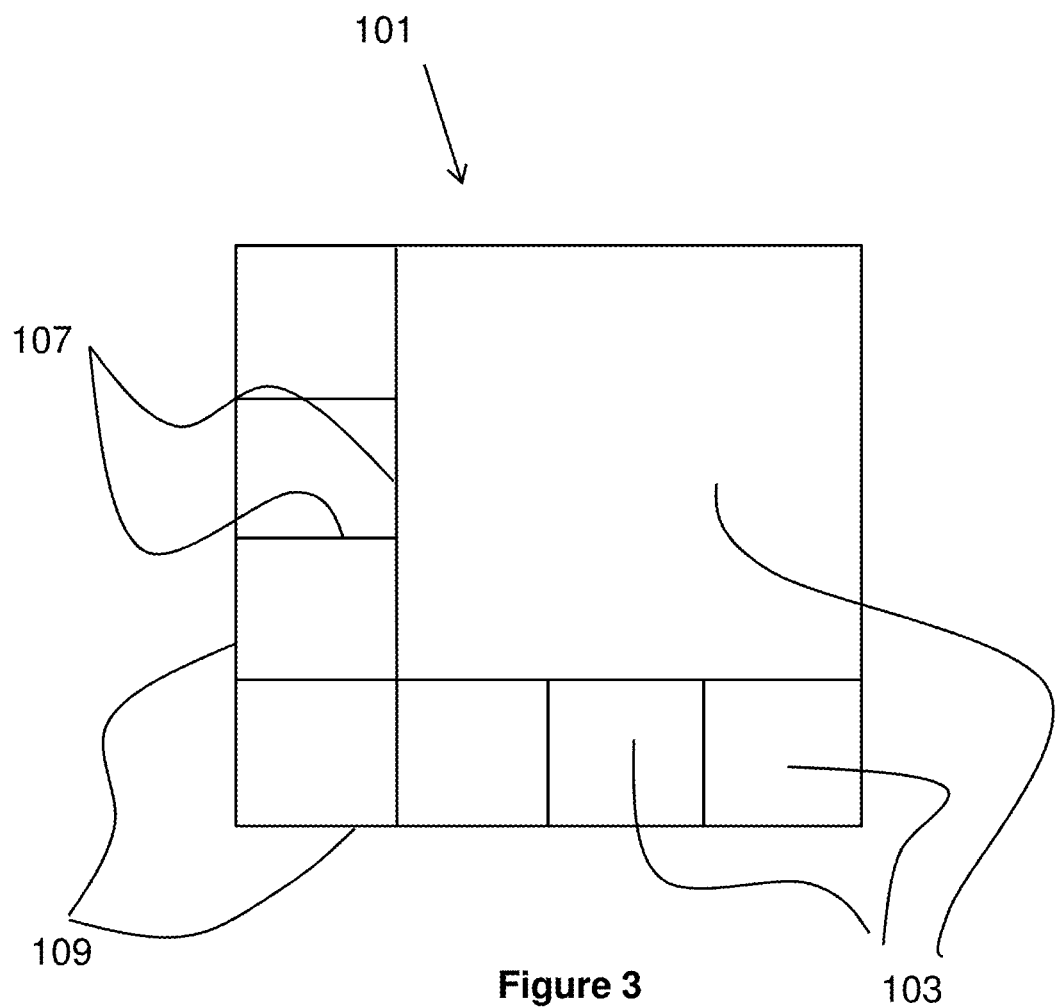
FIG. 3 shows a top view of an exemplary embodiment of a rectangular multi-compartment culture container of the invention.

Culture containers of the invention may comprise a bottom wall and at least one side wall coupled thereto. Side walls can be coupled to the bottom wall so that the side wall's planar surface is substantially transverse to the planar surface of the bottom wall. The culture container may have any number of side walls including 1, 2, 3, 4, 5, 6, 7, 8, 9, or 10 side walls. Side walls may be substantially straight or may be curved. The bottom wall may be a variety of shapes including, rectangular, circular, triangular, or pentagonal. The bottom wall shape should correspond to the number of side walls. For example, a container 101 with circular bottom wall 105 would comprise a single side wall 109, with a curved planar surface so that the bottom edge of the single side wall 109 forms a circle of substantially equal radius to that of the bottom wall 105 to which it is coupled as shown in FIG. 1. Alternatively, a container may have 4 straight side walls 109 coupled to a substantially rectangular bottom wall 105 as shown in FIG. 3. In embodiments having more than one side wall 109, the side walls may be coupled together at a vertical edge to form a corner as shown in FIG. 3.

Containers of the invention may include one or more interior walls which can divide the interior volume of the container into two or more compartments. Interior walls may be curved or straight and can be coupled to the bottom wall so that their planar surface is substantially transverse to the planar surface of the bottom wall. Interior walls can be coupled to the same planar surface of the bottom wall as the side walls. Interior walls may be coupled to one or more side walls and/or one or more other interior walls. A culture container may have any number of interior walls, including 1, 2, 3, 4, 5, 6, 7, 8, 9, or 10 interior walls and may comprise any number of compartments including 1, 2, 3, 4, 5, 6, 7, 8, 9, 10, or 11 compartments.

FIG. 1 illustrates an exemplary embodiment of a circular, multi-compartment culture container 101 having a circular bottom wall 105 and a single, curved side wall 109. The container 101 has a single curved interior wall 107, coupled to the bottom wall 105 to define a cylindrical center compartment 103. The container 101 also has several straight interior walls 107 coupled to both the curved side wall 109 and the curved interior wall 107, forming spokes and defining 10 smaller radial compartments 103 for a total of 11 compartments 103.

Figure 2:
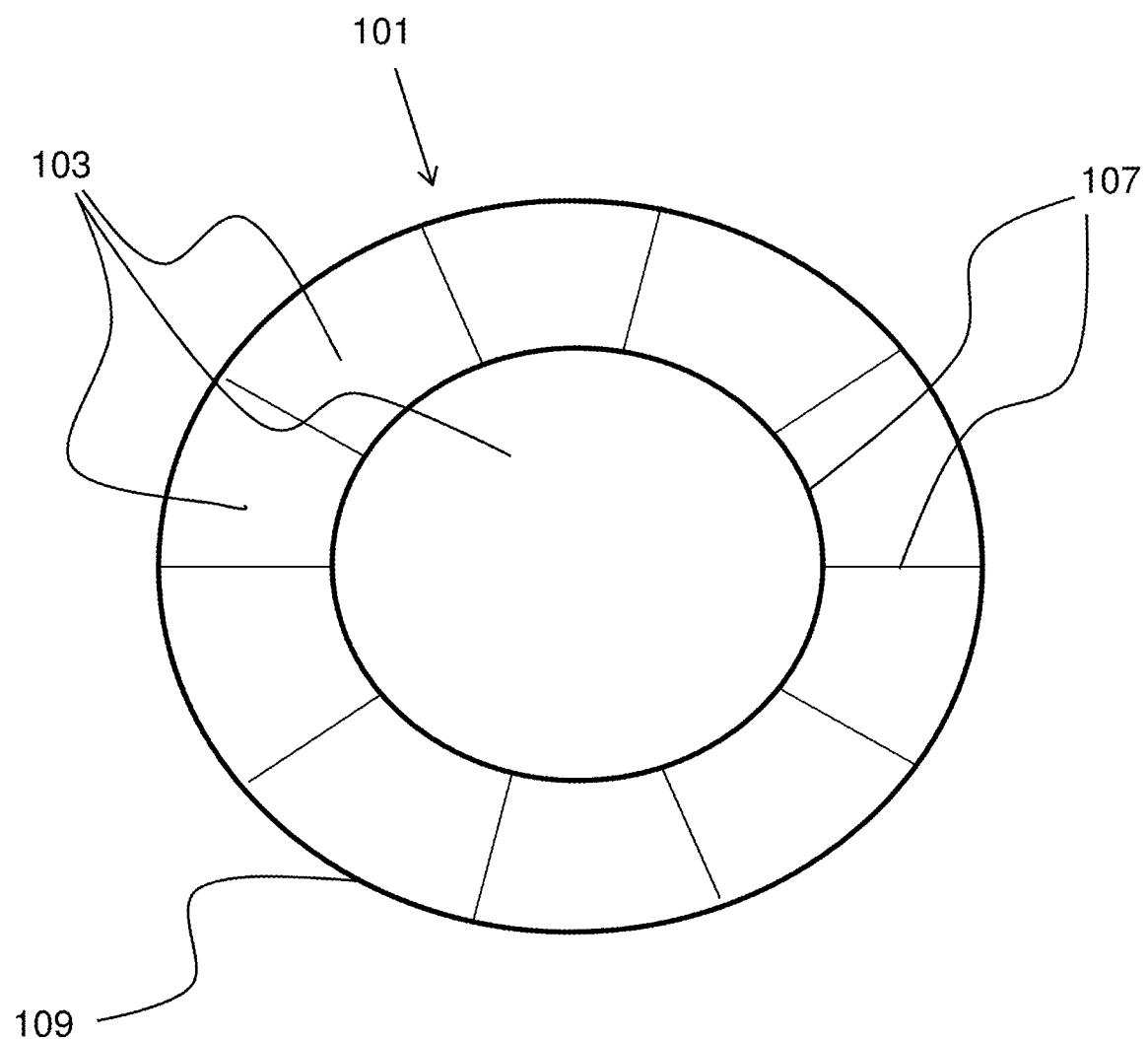
FIG. 2 shows a top view of an exemplary embodiment of a circular multi-compartment culture container of the invention.

FIG. 2 illustrates a birds-eye view of the circular, multi-compartment culture container 101 of FIG. 1, having 10 compartments 103 defined by a curved side wall 109, a curved interior wall 107 and 10 straight interior walls 107.

FIG. 3 shows a birds-eye view of an exemplary container 103 having a rectangular bottom wall and 4 side walls 109 defining 8 compartments including 1 larger compartment 103 and 7 smaller compartments.

The larger center compartment 103 of the containers 101 shown in FIGS. 1-3 may be sized to contain a larger piece of tissue for implantation while smaller surrogate tissues may be contained in the smaller surrounding compartments 103.

Figure 6A:
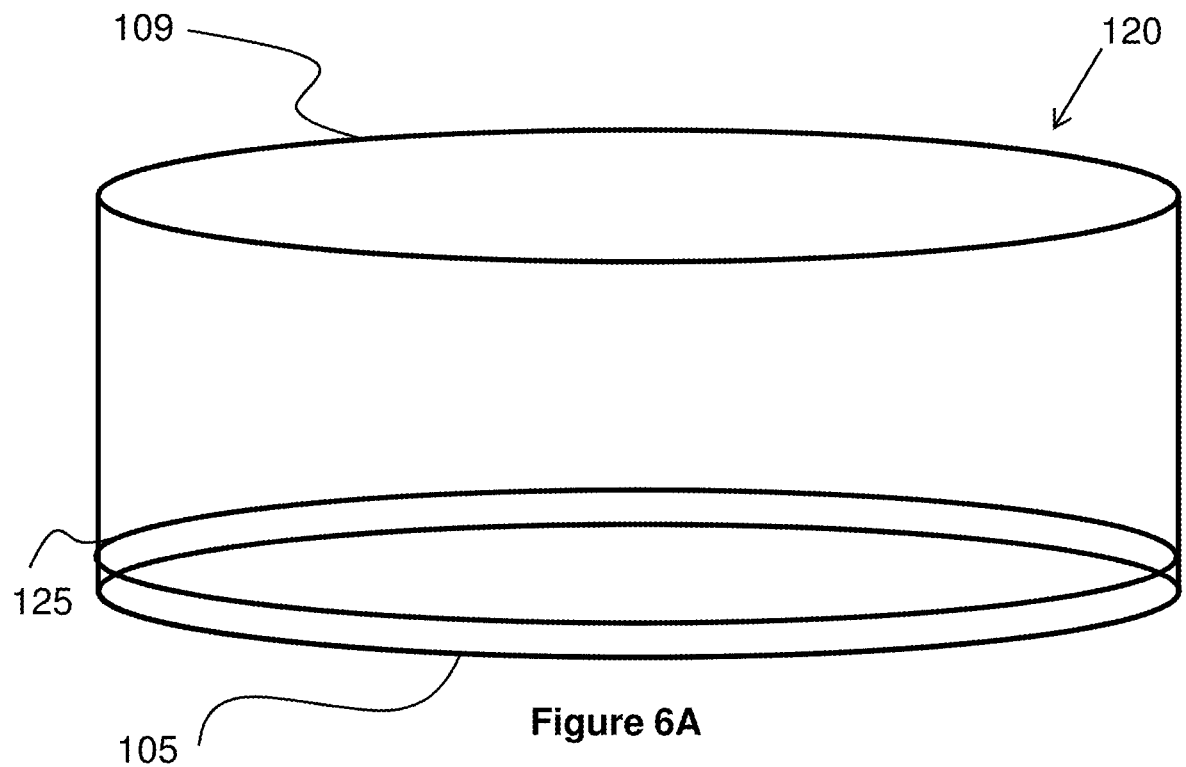
FIGS. 6A and 6B show an exemplary embodiment of a two component multi-compartment circular culture container.
Figure 6B:
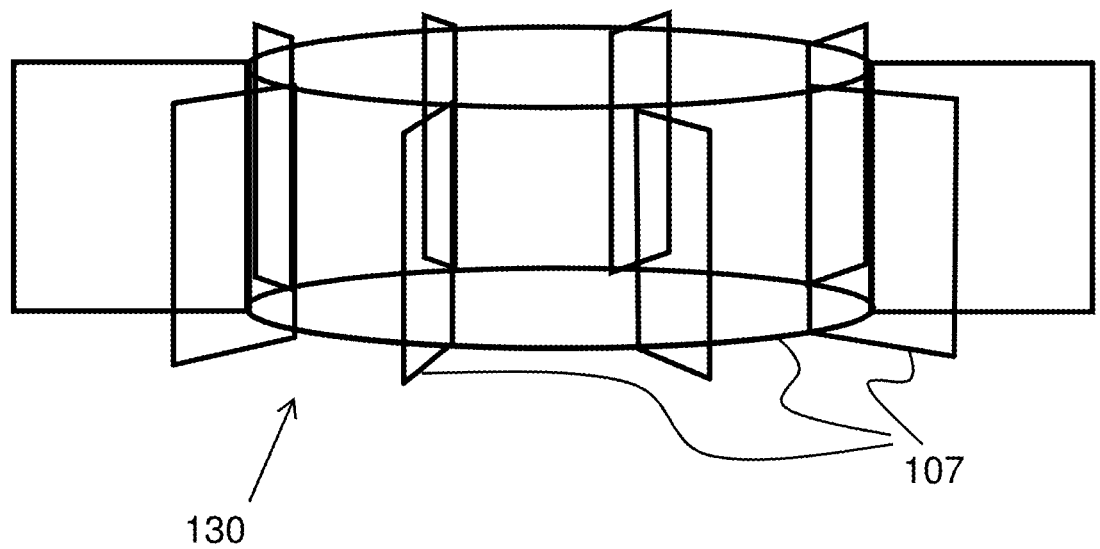

In certain aspects, the container may comprise multiple components such as a first unit comprising a bottom wall and at least one side wall and a second unit comprising one or more of the interior walls or partition so that the partition may be removed from the container providing a single compartment or inserted into the container to provide multiple compartments therein. One or more of the components may have slots or other physical mechanisms configured to accept a portion of the other component. FIGS. 6A and 6B depict an exemplary embodiment of a multi-component container. A first component 120 is shown in FIG. 6A comprising a single, curved side wall 109 coupled at its bottom edge to a circular bottom wall 105. FIG. 6B illustrates a second component 130 comprising a single, circular interior wall 107 and 10 straight interior walls 107 extending radially therefrom. The second component 130 is configured to be placed within the first component 120 in order to separate the interior volume of the first component into 10 compartments. The second component 130 may be dimensioned so that the radial edges of the straight side walls 107 form a tight fit with the inner planar surface of the curved side wall 109 when the two components are combined.

In certain instances, a single first component comprising the one or more side walls and the bottom wall may be compatible with multiple different second components comprising interior walls in various configurations so that, by interchanging second components, the number of compartments may be varied.

The first component may include a stop 125 as illustrated in FIG. 6A configured to prevent the bottom edge of the interior walls 107 from contacting the interior planar surface of the bottom wall 105.

In order to achieve fluid communication between the compartments of the container, the interior walls may have openings. In certain embodiments the openings may be dimensioned so as to allow fluid to pass between the compartments of the container without allowing cells, tissues, or 3D scaffolds to pass therebetween. In some aspects an interior wall may be perforated with one or more holes or pores. In such instances, each hole should have a diameter smaller than the largest dimension of the cell, tissue, or 3D scaffold being cultured within a compartment defined in part by that interior wall. For example, for 3D tissue culture scaffolds having a 4 mm diameter by 1.5 mm thickness, openings in the interior walls may have diameters less than 4 mm as the scaffolds should be unable to pass through an opening with a diameter less than 4 mm. In certain aspects, an interior wall may comprise a slit of a certain length and width. In such instances, one of the length or the width of the slit should be less than the smallest dimension of the cell, tissue, or 3D scaffold being cultured within a compartment defined in part by that interior wall. For example, using 3D tissue culture scaffolds having a 4 mm diameter by 1.5 mm thickness, the length or width of the slit may be any value so long as the other dimension is less than 1.5 mm.

Openings may be located at a variety of positions within an interior wall including near the center, top, or sides of an interior wall. Openings may be uniformly or differentially located on each interior wall. In certain instances, an opening in an interior wall may be located near the bottom wall of the container. Cell and tissue cultures may rest on the bottom wall of the container during the culturing process. Openings near the bottom wall can allow for the exchange, between compartments, of fluid, nutrients, growth factors, and other particles at the tissue level. Particles that may tend to settle to the bottom may be better exchanged through openings near the bottom wall, thus better replicating the culture environment across compartments.

Figure 4:
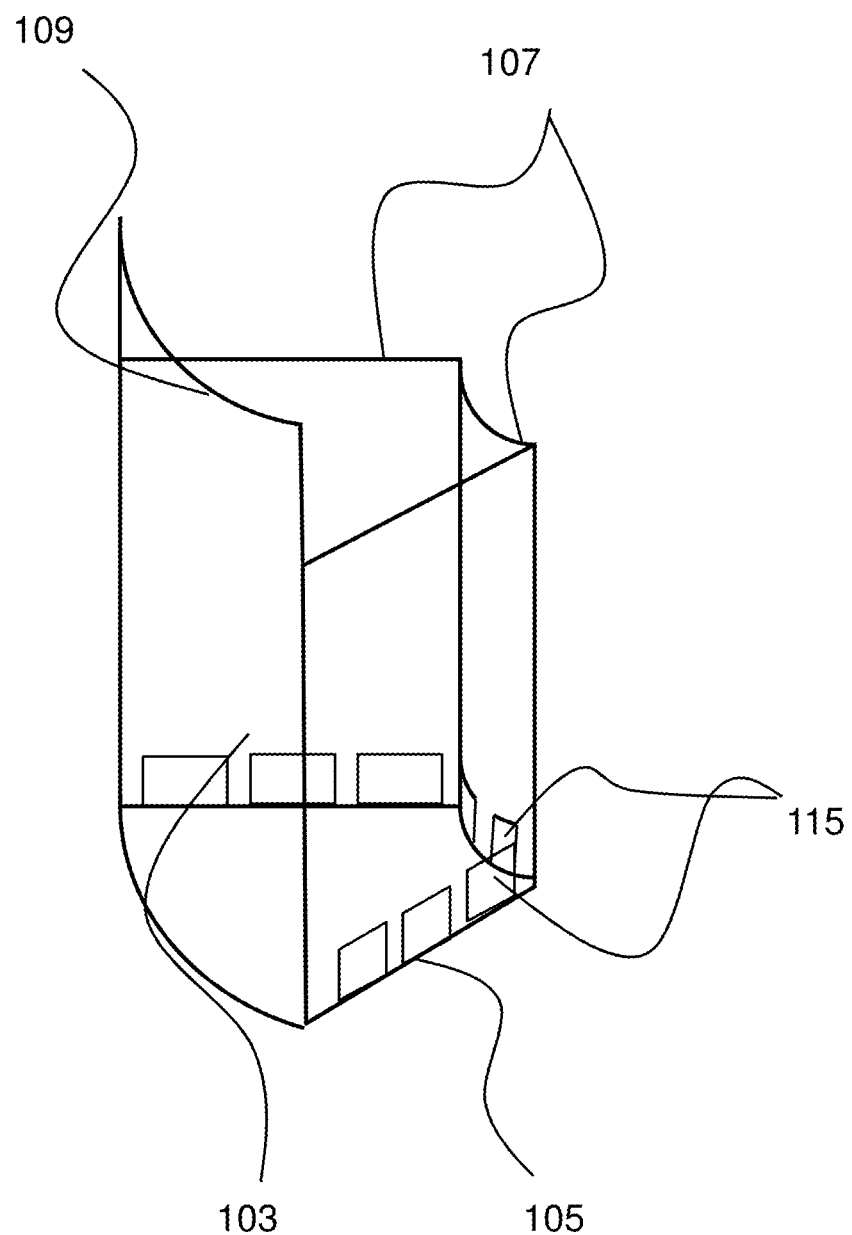
FIG. 4 shows a close up view of a single compartment of an exemplary embodiment of a circular multi-compartment culture container.

FIG. 4 illustrates an exemplary embodiment of a compartment 103 within a larger, cylindrical container such as the container 101 illustrated in FIG. 1. The compartment 103 in FIG. 4 is defined by a portion of a curved side wall 109, a portion of a curved interior wall 107, two straight interior walls 107, and a portion of a circular bottom wall 105. Each of the interior walls 107 has one or more openings 115 near the bottom wall enabling the passage of fluid between the compartment 103 and other, surrounding compartments (not shown). As noted above, the openings 115 may be dimensioned to allow fluid to pass through but to restrict the passage of the cultured cell or tissue within the compartment 103. In certain aspects, openings between compartments, in interior walls, may be covered by screens or filters configured to restrict inter-compartment passage of cells tissues or 3D scaffolds. In such instances the screen or filter may be of a biocompatible material and configured, by material, conformation, or surface treatment, to deter adherence of a cell or tissue thereto during the culturing process.

Interior walls and side walls may be substantially the same height relative to the bottom wall. In some aspects, the interior walls may have a height, relative to the bottom wall, that is less than the height of the side wall, relative to the bottom wall. In such instances, cell-culture medium or other fluid may be added to the container to a level, h, greater than the height of the interior walls but less than the height of the side walls so that the compartments are in fluid communication with each other. In certain aspects, one or more of the interior walls may be coupled to the side walls but not coupled to the bottom wall, leaving a gap between the bottom edge of the one or more interior walls and the planar surface of the bottom wall. This gap can be sized to allow fluid to pass between the compartments of the container without allowing cells, tissues, or 3D scaffolds to pass therebetween. In multi-component embodiments such as illustrated in FIGS. 6A and 6B, the stop 125 may be spaced from the bottom wall 125 so that, when the components are combined, a gap is left between the bottom edge of the one or more interior walls and the planar surface of the bottom wall. This gap can be sized to allow fluid to pass between the compartments of the container without allowing cells, tissues, or 3D scaffolds to pass therebetween. Fluid can be added to a level above or below the height of the interior walls. Fluid may be maintained at a level below the height of the interior walls in order to maintain separation of 3D scaffolds, cells, and tissues that may float to the surface of a fluid during culturing.

Figure 7:
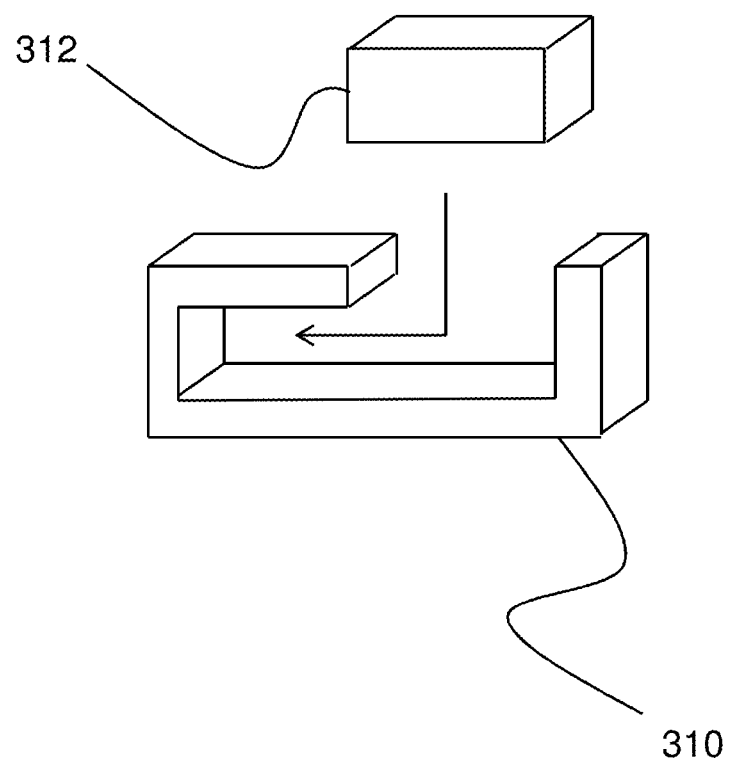
FIG. 7 shows an exemplary embodiment of interlocking tabs.
Figure 8:
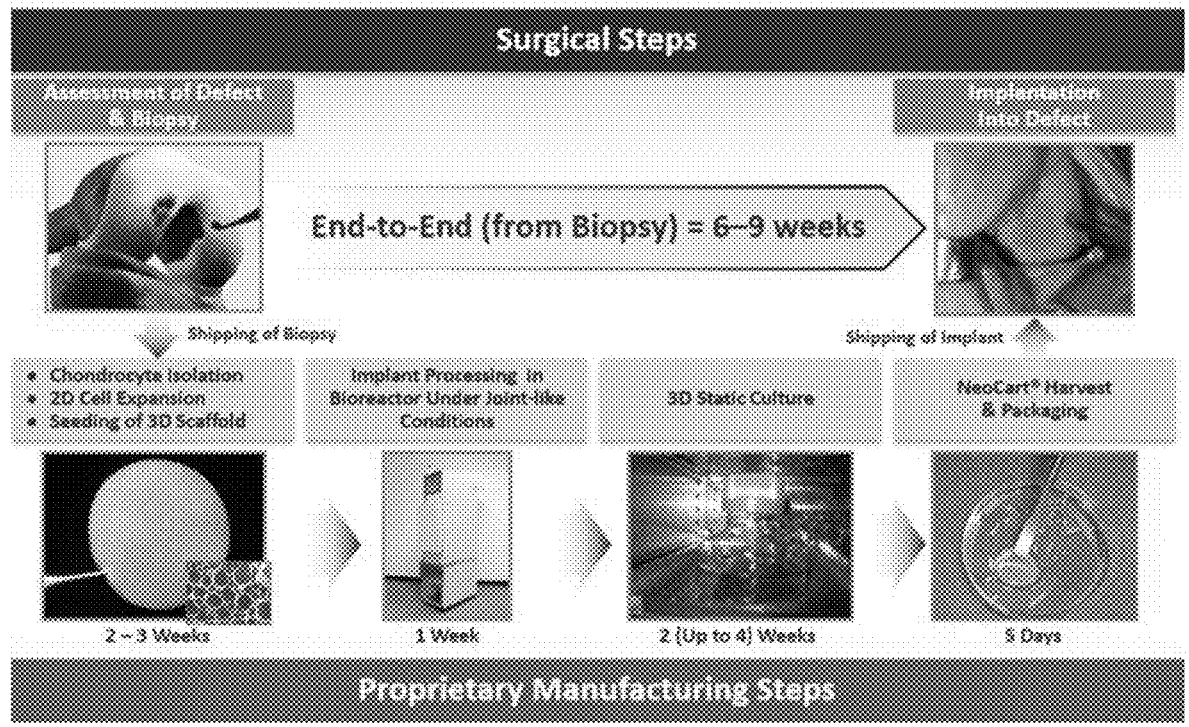
FIG. 8 shows an exemplary method for 3D culture of neo-cartilage for implantation.

In certain embodiments, devices of the invention include a lid configured to detachably couple to the top edge of the one or more side walls in order to enclose the container. The lid can generally correspond in shape and size to the bottom wall. In embodiments where the one or more side walls taper in or out from the edges of the bottom wall, the lid may be smaller or larger than the bottom wall and can generally correspond to the shape and size formed by the top edge of the one or more side walls. The lid may be configured to form an air or water-tight seal when detachably coupled to the container. In certain aspects, a lid and a container may comprise complementary or interlocking threads so that the lid may be screwed down onto the upper edge of the at least one side wall. In some embodiments the lid or the upper edge of the at least one side wall may comprise a recess configured to accept a gasket wherein the gasket is compressed when the lid is detachably coupled to the container and may thereby form a seal. The gasket may be constructed from any suitable material including rubber, plastic, metal, nylon, neoprene, or cork. In certain aspects, a lid may detachably couple to a container through engagement of interlocking tabs on the lid and container. Interlocking tabs may include snap-fit style cantilever prong and recess type connections as well as screw-type interlocking tabs. FIG. 7 illustrates an exemplary style of interlocking tab wherein the lid or the container may include a block 312 while the other includes a receptacle 310 configured to receive and lock in the block 312. The interlocking tabs illustrated in FIG. 7 may be engaged by pushing the lid onto the container and then twisting the lid relative to the container so that the block 312 is inserted down and then into the receptacle 310 as illustrated by the arrow in FIG. 7.

In certain aspects, the one or more side walls of a container may be coupled to the bottom wall of the container at substantially right angles and/or the container configured so that the opening at the top of the container has an area substantially equal to the area of the bottom wall. An opening may thusly be configured to provide unfettered access to each compartment within the container from directly above to facilitate manipulation of materials within each compartment without interference from a tapered or flask-like neck or opening.

In some aspects, a lid may comprise a vent and/or a gas permeable membrane of a size and shape configured to allow gas to pass into and out of a sealed container while restricting undesirable particles such as bacteria, endotoxins, and other contaminants. The lid may be configured so that, when detachably coupled to the container, the only avenue for gas exchange between the interior and exterior of the container is through the filter. The filter may have a variety of reference pore sizes including 0.2 to 3 gm such as 0.2, 0.5, 1, 1.5, 2, 2.5, or 3 gm. The filter may be of a variety of different materials such as cellulose, nylon, polytetrafluorethylene, polydimethylsiloxane (PDMS silicone), or glass fiber. Commercially available filter materials include, for example, ePTFE membrane from W. L. Gore & Associates, Inc., 555 Paper Mill Road, Newark, Del. 19711. A filter may also be located on a side wall of the container.

Figure 5A:
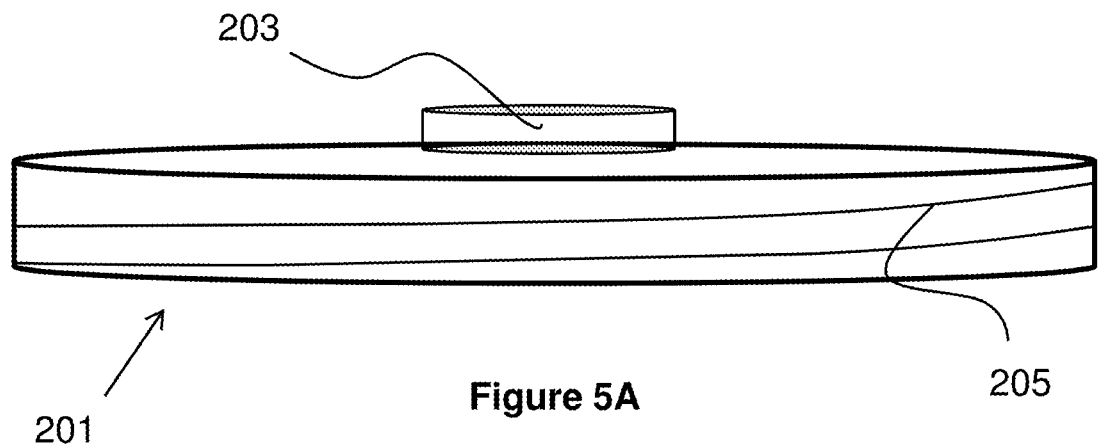
FIG. 5A shows a side view of an exemplary embodiment of a lid for a circular culture container.
Figure 5B:
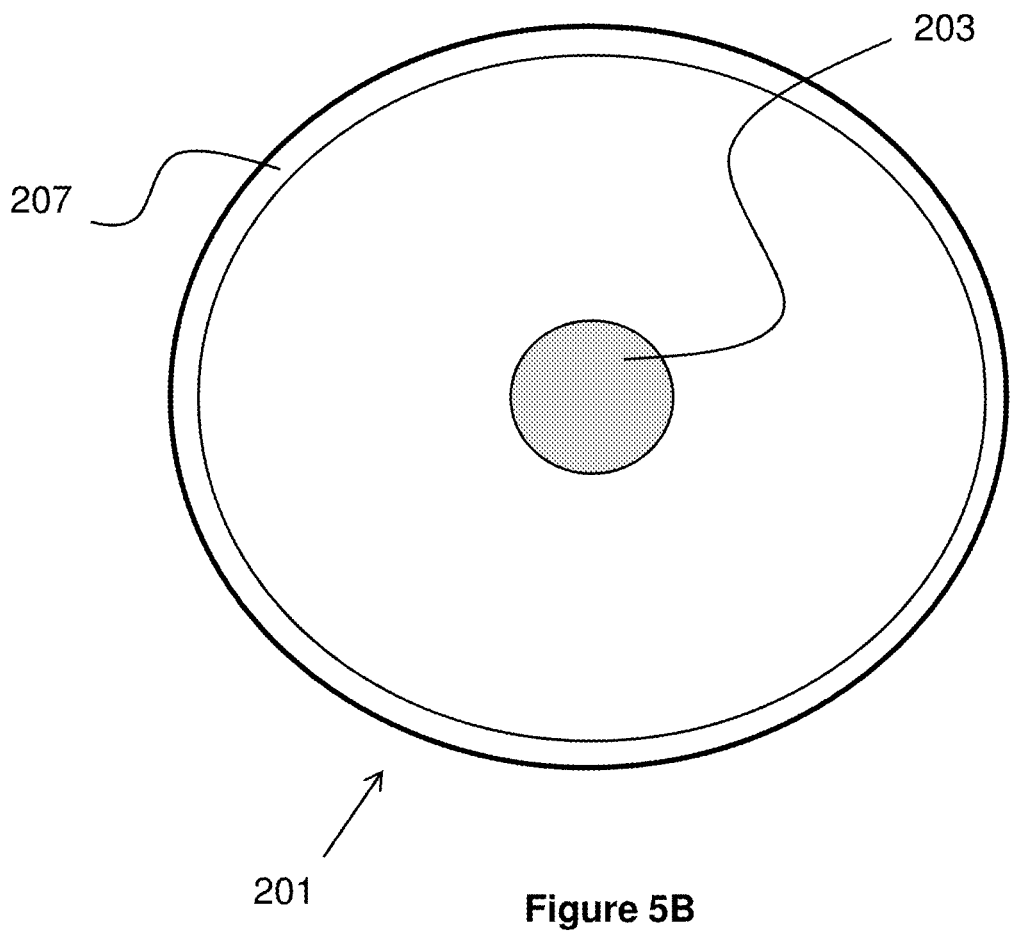
FIG. 5B shows a top view of an exemplary embodiment of a lid for a circular culture container.

FIGS. 5A and 5B show an exemplary embodiment of a lid 201 according to the invention. The lid 201 is substantially circular and configured to detachably couple to a substantially cylindrical container such as the container 101 shown in FIG. 1, 2, or 6A. The lid shown in FIGS. 5A and 5B comprises a circular filter 203 placed in the center of the lid. A lid filter may be part of a vent mechanism which includes a cap covering the filter material so that gas is vented through the side of the vent and the filter material is protected from fluid splashing. The lid shown in FIGS. 5A and 5B also comprises a downward facing lip with threads 205 on the interior surface thereof configured to interact with complementary threads on an exterior surface of a curved side wall of a container to provide a sealed compression through a screw-type mechanism. FIG. 5B shows a gasket 207, held in a recess of the lid and configured to be compressed against the upper edge of a curved side wall of a container. In certain aspects, the top of the lid and/or the bottom of the container may be configured with interlocking tabs and/or spacers to allow for controlled stacking of containers wherein the top container is spaced above the bottom container so that a filter on the bottom container's lid is still exposed to the exterior atmosphere.

In certain embodiments, a container of the invention may be sized so that multiple containers may fit on a 7 inch by 14 inch incubator tray. A container may be sized to contain a certain volume of fluid including at least 1, 10, 50, 100, 250, 500, 750, or 1000 mL. In an exemplary embodiment, a container 101 of the type illustrated in FIGS. 1 and 2 may have an outer diameter of 6 inches while the curved side wall 109 has a height of 2 inches and the interior walls 107 have a height of 1.5 inches and the single, curved interior wall forms a compartment 103 with an inside diameter of 3.5 inches. In an exemplary embodiment of a container of the type illustrated in FIG. 3, the container 101 has outside dimensions of 5 inches by 5 inches and the 4 side walls 109 have a height of 2 inches while the interior walls have a height of 1.5 inches. The interior walls 107 form one 3.75 inch by 3.75 inch compartment 103 and 7 1.25 inch by 1.25 inch compartments. In both of the above embodiments, two of the specified containers may fit on a single 7 inch by 14 inch incubator tray.

In certain embodiments, the lid, the container, or components thereof may comprise a variety of materials. Materials may be biocompatible, endotoxin-free, and/or configured to be sterilized to a variety of Sterility Assurance Levels (SAL) including $10^{-1}$, $10^{-2}$, $10^{-3}$, $10^{-4}$, $10^{-5}$, or $10^{-6}$, for example. In some embodiments, the lid, container, and/or components thereof may comprise a USP Class N, V, or VI material, including, for example, polypropylene, high-density polyethylene, polystyrene, styrene-acrylonitrile (SAN), polycarbonatestyrene-maleic anhydride (SMA), cyclic olefin copolymers (COC), acrylic, acrylic-polyvinyl chloride alloys, polypropylene copolymers, polysulfone, polymethylpentene, or cellulosic. The lid, the container, or components thereof may comprise a substantially transparent material to allow visual inspection of the container's contents from outside of the container. Containers and lids may be configured as single-use disposables or may be configured for repeated use and sterilization. Containers and lids can comprise materials which are nonreactive to standard cell culture media such as EMEM or DMEM.

In some aspects, the interior surface of the bottom wall, the interior surface of the one or more side walls, and/or the surfaces of the one or more interior walls may be smooth; textured with ridges, valleys, pores, or dimples; and/or treated with an agent to deter adherence of cultured cells or tissues and/or the facilitate retrieval from the container by scooping under the cultured tissue with a retrieval tool. In certain aspects, the interior surface of the side walls, interior walls, and/or bottom wall, may be treated with an antimicrobial agent or other instrument to prevent microbial growth and/or contamination.

The lid, the container, or components thereof may be produced by a variety of known means including extrusion, injection molding, blow molding, or rotational molding. The container may be formed from a single piece of material or from multiple pieces which are subsequently coupled together. The lid may be similarly formed. Where constructed from multiple pieces, the pieces maybe joined a variety of known techniques including welding, or bonding using a bonding agent such as a biocompatible adhesive.

In a preferred embodiment, the lid, container, or components thereof are made using thermoforming. In thermoforming, a sheet of material, such as polystyrene is heated until pliable and then formed to a desired shape using a mold. Vacuum pressure may be used to conform the material to the mold. The material may then be cooled to regain rigidity, and then removed from the mold. The resulting product may then be trimmed or otherwise finished to remove excess material or rough edges.

In some aspects, the lid, container, or portions thereof may be formed using injection molding. In injection molding, a mold block with a hollow cavity in shape of the desired product is coupled to a reservoir that can inject molten plastic resin is made. The mold is made in two halves such that a completed part can be removed from one of the halves without any portion being impeded by portions of the mold cavity. The mold is placed in a processing machine capable of clamping the two halves of the mold together. Molten plastic resin is injected into the cavity at high pressure in order to facilitate rapidly filling thin or distant volumes of the mold.

INCORPORATION BY REFERENCE

References and citations to other documents, such as patents, patent applications, patent publications, journals, books, papers, web contents, have been made throughout this disclosure. All such documents are hereby incorporated herein by reference in their entirety for all purposes.

EQUIVALENTS

Various modifications of the invention and many further embodiments thereof, in addition to those shown and described herein, will become apparent to those skilled in the art from the full contents of this document, including references to the scientific and patent literature cited herein. The subject matter herein contains important information, exemplification and guidance that can be adapted to the practice of this invention in its various embodiments and equivalents thereof.

The invention claimed is:

1. A method for culturing a tissue comprising:
providing a container comprising a bottom wall coupled to a bottom edge of at least one side wall, and an at least one interior wall coupled to the at least one side wall to define at least a first compartment and a second compartment within the container, wherein the at least one interior wall comprises a bottom edge that does not contact the bottom wall, leaving a gap between the bottom wall and the at least one interior wall, wherein the gap allows fluid to pass between the first and second compartments without allowing cells, tissues, or 3D scaffolds to pass therebetween;
providing a lid comprising a gas-permeable membrane, wherein the lid is configured to be detachably coupled to a top edge of the at least one side wall;
introducing a first living cell of a first cell type to the first compartment and a second living cell of a second cell type to the second compartment in the presence of a cell culture medium;
exposing the container to conditions promoting cell growth to produce a first tissue from the first living cell and a second tissue from the second living cell.

2. The method of claim 1, wherein the first cell type or the second cell type is a chondrocyte, mesenchymal stem cell, fibroblast, osteocyte, osteoblast, synoviocyte, induced pluripotent stem cell (iPSC), embryonic stem cell (ESC), lymphocyte, adipocyte, myofibroblast, hepatocyte, islet cell, monocyte, endometrial regenerative cell, or cancer stem cell.

3. The method of claim 2, wherein the first cell type is a chondrocyte.

4. The method of claim 3, wherein the first tissue is neo-cartilage.

5. The method of claim 2, wherein the second cell type is a chondrocyte.

6. The method of claim 5, wherein the second cell type is neo-cartilage.

7. The method of claim 1, wherein the first living cell or the second living cell is present on the bottom wall of the container.

8. The method of claim 1, wherein the exposing step comprises adding a fluid to a level below the height of the at least one interior wall.

9. The method of claim 1, further comprising seeding a 3D scaffold with the first living cell and introducing the 3D scaffold seeded with the first living cell into the first compartment.

10. The method of claim 1, further comprising preparing the first tissue for implantation into a human body.

11. The method of claim 1, further comprising performing testing on the second tissue to verify viability of the first tissue.

12. The method of claim 1, wherein the lid or the container comprises polypropylene, high-density polyethylene, polystyrene, styrene-acrylonitrile (SAN), polycarbonatestyrene-maleic anhydride (SMA), cyclic olefin copolymers (COC), acrylic, acrylic-polyvinyl chloride alloys, polypropylene copolymers, polysulfone, polymethylpentene, or cellulosic.

13. The method of claim 1, wherein the container comprises a circular bottom wall, a circular lid, and a single, curved sidewall coupled thereto to form a substantially cylindrical shape.

14. The method of claim 1, wherein the container comprises at least 3 compartments.

15. The method of claim 1, wherein the at least one side wall has a first height relative to the bottom wall that is substantially equal to a second height of the at least one interior wall relative to the bottom wall.

16. The method of claim 1, wherein the gas-permeable membrane comprises a 0.2 micron filter.

17. The method of claim 1, wherein the container is configured to hold at least 500 mL of fluid.

* * * * *